US006525053B1

(12) United States Patent
Black

(10) Patent No.: US 6,525,053 B1
(45) Date of Patent: *Feb. 25, 2003

(54) PROSTAGLANDIN ENDOPEROXIDE H SYNTHASE BIOSYNTHESIS INHIBITORS

(75) Inventor: Lawrence A. Black, Libertyville, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/137,403

(22) Filed: Aug. 20, 1998

Related U.S. Application Data

(60) Provisional application No. 60/056,652, filed on Aug. 22, 1997.

(51) Int. Cl.$^7$ ..................... A61K 31/50; C07D 237/14; C07D 237/16

(52) U.S. Cl. ................. 514/247; 514/85; 544/232; 544/238; 544/239; 544/240; 544/241

(58) Field of Search ................ 544/239, 238, 544/240, 241, 232; 514/247, 85

(56) References Cited

U.S. PATENT DOCUMENTS

| | | | |
|---|---|---|---|
| 4,404,203 A | * 9/1983 | Sircar | .......... 514/247 |
| 5,474,995 A | 12/1995 | Ducharme et al. | |
| 5,521,207 A | 5/1996 | Graneto | |
| 5,580,985 A | 12/1996 | Lee et al. | |
| 5,622,948 A | 4/1997 | Dunn et al. | |
| 6,004,960 A | * 12/1999 | Li et al. | ........ 544/239 |
| 6,307,047 B1 | * 10/2001 | Black et al. | ......... 544/240 |
| 2002/0028938 A1 | * 3/2002 | Black et al. | ......... 544/238 |

FOREIGN PATENT DOCUMENTS

| | | |
|---|---|---|
| EP | 0400519 | 5/1990 |
| WO | 9500501 | 1/1995 |
| WO | 9610012 | 4/1996 |
| WO | 9616934 | 6/1996 |
| WO | 9621662 | 7/1996 |
| WO | 9624584 | 8/1996 |
| WO | 9624585 | 8/1996 |
| WO | 9625405 | 8/1996 |
| WO | 9631509 | 10/1996 |
| WO | 9636617 | 11/1996 |
| WO | 9636623 | 11/1996 |
| WO | 9637476 | 11/1996 |
| WO | 9714691 | 4/1997 |
| WO | 9841511 | * 9/1998 |
| WO | 9910331 | * 3/1999 |
| WO | 9914194 | 3/1999 |

OTHER PUBLICATIONS

Griswold et al., *Medicinal Research Reviews*, 16 p. 181–206 (1996).*

Vane, *Nature*, vol. 367, p. 215–216 (1994).*

Battistini, B., et al., "COX–1 and COX–2: Toward the Development of More Selective NSAIDs", *DN&P*, 7(8):501–512 (1994).

Bertenshaw, S.R., et al., "Conformationally Restricted 1,5–Diarylpyrazoles are Selective COX–2 Inhibitors", *Bioorganic & Medicinal Chemistry Letters*, 23:2827–2830 (1996).

Cashman, J.N., "The Mechanisms of Action of NSAIDs in Analgesia", *Drugs*, 52(5):13–23 (1996).

Cho, S–D., "Concurrent Alkylation–Methoxylation of 4,5–Dihalopyridazin–6–ones and Synthesis of 5–Halo–4–hydroxypyridazin–6–ones", *J. Heterocyclic Chem.*, 33:1579–1582 (1996).

DeWitt, D.L., "The Differential Susceptibility of Prostaglandin Endoperoxide H Synthases–1 and –2 to Nonsteroidal Anti–inflammatory Drugs: Aspirin Derivatives as Selective Inhibitors", *Med. Chem. Res.*, 5:325–343 (1995).

Freisen, R.W., "Novel 1,2–Diarylcyclobutenes: Selective and Orally Active Cox–2 Inhibitors", *Bioorganic & Medicinal Chemistry Letters*, 6(22):2677–2682 (1996).

Gauthier, J.Y., "Synthesis and Biological Evaluation of 2,3–Diarylthiopenes as Selective COX–2 Inhibitors. Part II. Replacing the Heterocycle", *Bioorganic & Medicinal Chemistry Letters*, 6(1):87–92 (1996).

Huang, H–C, "Diaryl Indenes and Benzofurans: Novel Classes of Potent and Selective and Cyclooxygenase–2 Inhibitors", *Bioorganic & Medicinal Chemistry Letters*, 5(20):2377–2380 (1995).

Kurumbail, R.G., et al., "Structural basis for selective inhibition of cyclooxygenase–2 by anti–inflammatory agents", *Nature*, 384(19/26):644–648 (1996).

Li, J.J., et al., "1,2–Diarylcyclopentenes as Selective Cyclooxygenase–2 Inhibitors and Orally Active Anti–inflammatory Agents", *J. Med. Chem.*, 38(22):4570–4578 (1995).

Li, J.J., et al., "Novel Terphenyls as Selective Cyclooxygenase–2 Inhibitors and Orally Active–inflammatory Agents", *J. Med. Chem.*, 39:1846–1856 (1996).

(List continued on next page.)

Primary Examiner—Emily Bernhardt
(74) *Attorney, Agent, or Firm*—Michael J. Ward; Portia Chen

(57) ABSTRACT

The present invention describes pyridazione compounds having the formula (I), which are cyclooxygenase (COX) inhibitors The compounds are selective inhibitors of cyclooxygenase-2-(COX-2), which is the inducible isoform associated with inflammation, as opposed to the constitutive isoform, cyclooxygenase-1 (COX-1), which is an important "housekeeping" enzyme in many tissues, including the gastrointestinal (GI) tract and the kidneys. The selectivity of these compounds for COX-2 minimizes the unwanted GI and renal side-effects seen with currently marketed non-steroidal anti-inflammatory drugs (NSAIDS).

4 Claims, No Drawings

OTHER PUBLICATIONS

Mitchell, J.A., "Cyclooxygenase–2: Regulation and Relevance in Inflammation", *Biochemical Pharmacology*, 50(10):1535–1542 (1995).

Nannini, G., et al., "Synthesis and pharmacological activity of some 5, 6–diphenyl–pyridazines", *Eur. J. Med. Chem.*, 14(1):53–60 (1979).

Penning, T.D., et al., Synthesis and Biological Evaluation of the 1,5–Diarylpyrazole Class of Cyclooxygenase–2 Inhibitors: Identification of 4–[5–(4–Methylphenyl)–3–(trifluoromethyl)–1H–pyrazol–1–yl]benzenesulfonamide (SC–58635, Celecoxib), *J. Med. Chem.*, 40:1347–1365 (1997).

Pinto, D.J.P., et al., "Chemistry and Pharmacokinetics of Diarylthiophenes and Terphenyls as Selective Cox–2 Inhibitors[1]", *Bioorganic & Medicinal Chemistry Letters*, 6(24):2907–2912 (1996).

Reitz, D.B., et al., "Novel 1,2–Diarylcyclopentenes are Selective, Potent, and Orally Active Cyclooxygenase Inhibitors", *Med. Chem. Res.*, 5:351–363 (1995).

Carruthers, N.I., et al.,"Selective Cyclooxygenase Inhibitors", *Chemtracts–Organic Chemistry*, 8:273–276 (1995).

Reitz, D.B., et al., "Selective Cyclooxygenase Inhibitors: Novel 4–Spiro 1,2–Diarylcyclopentenes are Potent and Orally Active COX–2 Inhibitors", *Bioorganic & Medicinal Chemistry Letters*, 5(8):867–872 (1995).

Thérien, M., "Synthesis and Biological Evaluation of 5,6–Diarylimidazo [2.1–b]Thiazole as Selective COX–2 Inhibitors", *Bioorganic & Medicinal Chemistry Letters*, 7(1):47–52 (1997).

Wilkerson, W.W., et al., "Antiinflammatory 4,5–Diarylpyrroles. 2. Activity as a Function of Cyclooxygenase–2 Inhibition", *J. Med. Chem.*, 38:3895–3901 (1995).

Wilkerson, W.W., et al., "Antiinflammatory 4,5–Diarylpyrroles: Synthesis and QSAR", *J. Med. Chem.*, 37:988–998 (1994).

Wong, E., et al., "Conversion of Prostaglandin G/H Synthase –1 into an Enzyme Sensitive to PGHS–2–selective Inhibitors by a Double $His^{513} \rightarrow Arg$ and $Ile^{523} \rightarrow Val$ Mutation*", *Journ of Biol. Chem.*, 272(14):9280–9285 (1997).

Browner, M., "X–ray crystal structure of human COX–2", *Roche Bioscience*.

Frenette, R., et al., "Novel 1,2–Diarylcyclobutenes: Selective and Orally Active COX–2 Inhibitors", *Merck Frosst Center for Therapeutic Research*.

Ford–Hutchinson, A.W., "COX–2 inhibitors", *Merck Frosst Center for Therapeutic Research*.

Gierse, J.K., et al., "A Single Amino Acid Difference Between COX–1 and 2 Reverses the Selectivity of COX–2 Specific Inhibitors", *Monsanto/Searle Research*, p. 40.

Magolds, R.L., "Structure–Activity–Relationship (SAR) with a Novel Serles of Selective Cyclooxygenase–2 Inhibitors", *Dupont Merck Pharmaceutical Company*, 1–4.

Handout from Poster Session, American Chemical Society National Meeting Boston, Ma, Aug. 23, 1998 "Pyridazinones as Selective Cyclooxygenase–2–Inhbitors", Li, Chun–Sing; Brideau, Christine; Chan, Chi Chung; Savoie, Chantal; Claveau, David; Charleson, Stella; Gordon, Robert; Greig, Gillian; Gauthier, Jacques Yves; Lau, Cheuk Kun; Riendeau, Denis; Therien, Michel; Wong, Elizabeth; Prasit, Petpiboon; Merck Frosst Session for Therapeutic Research, P.O. Box 1005, Pointe Claire–Dorval, Quebec, H9R, 4P8, Canada.

* cited by examiner

PROSTAGLANDIN ENDOPEROXIDE H SYNTHASE BIOSYNTHESIS INHIBITORS

This application claims the benefit of U.S. Provisional Application No. 60/056,652, filed Aug. 22, 1997.

TECHNICAL FIELD

The present invention encompasses novel pyridazinone compounds useful in the treatment of cyclooxygenase-2 mediated diseases. More particularly, this invention concerns a method of inhibiting prostaglandin biosynthesis, particularly the induced prostaglandin endoperoxide H synthase (PGHS-2, cyclooxygenase-2, COX-2) protein.

BACKGROUND OF THE INVENTION

The prostaglandins are extremely potent substances which produce a wide variety of biological effects, often in the nanomolar to picomolar concentration range. The discovery of two forms of prostaglandin endoperoxide H synthase, isoenzymes PGHS-1 and PGHS-2, that catalyze the oxidation of arachidonic acid leading to prostaglandin biosynthesis has resulted in renewed research to delineate the role of these two isozymes in physiology and pathophysiology. These isozymes have been shown to have different gene regulation and represent distinctly different prostaglandin biosynthesis pathways. The PGHS-1 pathway is expressed constitutively in most cell types. It responds to produce prostaglandins that regulate acute events in vascular homeostasis and also has a role in maintaining normal stomach and renal function. The PGHS-2 pathway involves an induction mechanism which has been linked to inflammation, mitogenesis and ovulation phenomena.

Prostaglandin inhibitors provide therapy for pain, fever, and inflammation, and are useful therapies, for example in the treatment of rheumatoid arthritis and osteoarthritis. The non-steroidal anti-inflammatory drugs (NSAIDs) such as ibuprofen, naproxen and fenamates inhibit both isozymes. Inhibition of the constitutive enzyme PGHS-1 results in gastrointestinal side effects including ulcers and bleeding and incidence of renal problems with chronic therapy. Inhibitors of the induced isozyme PGHS-2 may provide anti-inflammatory activity without the side effects of PGHS-1 inhibitors.

The problem of side-effects associated with NSAID administration has never completely been solved in the past. Enteric coated tablets and co-administration with misoprostol, a prostaglandin derivative, have been tried in an attempt to minimize stomach toxicity. It would be advantageous to provide compounds which are selective inhibitors of the induced isozyme PGHS-2.

The present invention discloses novel compounds which are selective inhibitors of PGHS-2.

SUMMARY OF THE INVENTION

The present invention discloses pyridazinone compounds which are selective inhibitors of cyclooxygenase-2 (COX-2). The the compounds of the present invention have the formula I:

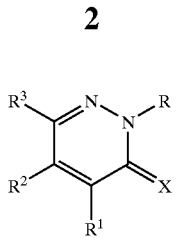

where
$X$ is selected from the group consisting of O, S, $NR^4$, $N—OR^a$, and $N—NR^bR^c$, wherein $R^4$ is selected from the group consisting of alkyl, alkenyl, cycloalkyl, cycloalkenyl, cycloalkylalkyl, cycloalkenylalkyl, aryl, heterocyclic, heterocyclic (alkyl), and arylalkyl; and $R^a$, $R^b$, and $R^c$ are independently selected from the group consisting of alkyl, cycloalkyl, cycloalkylalkyl, aryl, and arylalkyl;

$R$ is selected from the group consisting of hydrogen, alkyl, alkenyl, alkynyl, alkylcarbonylalkyl, alkylsulfonylalkyl, alkylsulfonylarylalkyl, alkoxy, alkoxyalkyl, carboxy, carboxyalkyl, cyanoalkyl, haloalkyl, haloalkenyl, haloalkynyl, hydroxyalkyl, cycloalkyl, cycloalkylalkyl, cycloalkenyl, cycloalkenylalkyl, aryl, arylalkyl, arylalkenyl, arylalkynyl, arylalkoxy, aryloxy, arylcarbonylalkyl, heterocyclic, heterocyclic (alkyl), heterocyclic (alkoxy), heterocyclic (oxy), $—C(O)R^5$, $—(CH_2)_nC(O)R^5$, $—R^6—R^7$, $—(CH_2)_nCH(OH)R^5$, $—(CH_2)_nCH(OR^d)R^5$, $—(CH_2)_nC(NOR^d)R^5$, $—(CH_2)_nC(NR^d)R^5$, $—(CH_2)_nCH(NOR^d)R^5$, $—(CH_2)_nCH(NR^dR^e)R^5$, $—(CH_2)_nC≡C—R^7$, $—(CH_2)_n[CH(CX'_3)]_m$ $—(CH_2)_n—CX'_3$, $—(CH_2)_n(C\ X'_2)_m—(CH_2)_n—CX'_3$, $—(CH_2)_n[CH(CX'_3)]_m—(CH_2)_n—R^8$, $—(CH_2)_n(C X'_2)_m—(CH_2)_nR^8$, $—(CH_2)_n(CHX')_m—(CH_2)_n—CX'_3$, $—(CH_2)_n(CHX')_m—(CH_2)_n—R^8$, and $—(CH_2)_n—R^{20}$, wherein $R^5$ is selected from the group consisting of alkyl, alkenyl, alkynyl, cycloalkyl, cycloalkenyl, aryl, arylalkyl, haloalkyl, haloalkenyl, haloalkynyl, heterocyclic, and heterocyclic (alkyl);

wherein $R^6$ is alkylene or alkenylene;

$R^7$ and $R^8$ are independently selected from the group consisting of hydrogen, alkyl, alkenyl, alkynyl, haloalkyl, cycloalkyl, cycloalkenyl, aryl, arylalkyl, heterocyclic, and heterocyclic (alkyl);

$R^{20}$ is selected from the group consisting of alkyl, alkenyl, haloalkyl, cycloalkyl, cycloalkenyl, aryl, heterocyclic, and heterocyclic (alkyl);

$R^d$ and $R^e$ are independently selected from the group consisting of hydrogen, alkyl, alkenyl, alkynyl, haloalkyl, cycloalkyl, cycloalkenyl, aryl, arylalkyl, heterocyclic, and heterocyclic (alkyl);

$X'$ is halogen;

n is from 0 to about 10, and m is 0 to about 5; at least one of $R^1$, $R^2$ and $R^3$ is a group, substituted with a substituent having a group $—X^1—R^9$, having the formula:

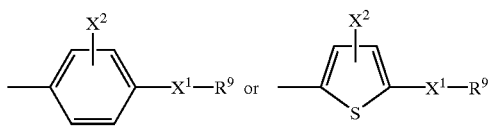

where $X^1$ is selected from the group consisting of $—SO_2—$, $—SO(NR^{10})—$, $—PO(OR^{11})—$, and $—PO(NR^{12}R^{13})—$, $R^9$ is selected from the group consisting of alkyl, alkenyl, alkynyl, cycloalkyl, cycloalkenyl, amino, —NHNH$_2$, alkylamino, dialkylamino, alkoxy, thiol, alkylthiol, and protecting groups, $X^2$ is selected from the group consisting of hydrogen or halogen;

$R^{10}$, $R^{11}$, $R^{12}$, and $R^{13}$ are independently selected from the group consisting of hydrogen, alkyl, and cycloalkyl, or $R^{12}$ and $R^{13}$ can be taken together, with the nitrogen to which they are attached, to form a heterocyclic ring having from 3 to 6 atoms.

The remaining two of the groups of $R^1$, $R^2$, and $R^3$, are independently selected from the group consisting of hydrogen, hydroxy, hydroxyalkyl, halogen, alkyl, alkenyl, alkynyl, alkoxy, alkoxyalkyl, amido, amidoalkyl, haloalkyl, cycloalkyl, cycloalkylalkyl, cycloalkenyl, cycloalkenylalkyl, amino, aminocarbonyl, aminocarbonylalkyl, alkylamino, dialkylamino, arylamino, arylalkylamino, diarylamino, aryl, heterocyclic, heterocyclic (alkyl), cyano, nitro, and —Y—$R^{14}$, wherein Y is selected from the group consisting of, —O—, —S—, —C($R^{16}$) ($R^{17}$)—, C(O)NR$^{21}$—, —C(O)—, —C(O)O—, —NH—, —NC(O)—, and —NR$^{19}$—. $R^{14}$ is selected from the group consisting of hydrogen, halogen, alkyl, alkenyl, alkynyl, hydroxy, cycloalkyl, cycloalkenyl, amino, cyano, aryl, arylalkyl, heterocyclic, and heterocyclic (alkyl), $R^{16}$, $R^{17}$, and $R^{19}$ are independently selected from the group consisting of alkyl, alkenyl, cycloalkyl, cycloalkenyl, alkoxy, aryl, arylalkyl, heterocyclic, heterocyclic (alkyl), or cyano; and $R^{21}$ is selected from the group consisting of hydrogen, alkyl, alkenyl, cycloalkyl, cycloalkenyl, alkoxy, aryl, arylalkyl, heterocyclic, heterocyclic (alkyl), or cyano; or a pharmaceutically acceptable salt, ester, or prodrug thereof.

DETAILED DESCRIPTION OF THE INVENTION

All patents, patent applications, and literature references cited in the specification are hereby incorporated by reference in their entirety. In the case of inconsistencies, the present disclosure, including definitions, will prevail.

The present invention discloses pyridazinone compounds which are cyclooxygenase (COX) inhibitors and are selective inhibitors of cyclooxygenase-2 (COX-2). COX-2 is the inducible isoform associated with inflammation, as opposed to the constitutive isoform, cyclooxygenase-1 (COX-1) which is an important "housekeeping" enzyme in many tissues, including the gastrointestinal (GI) tract and the kidneys.

In one embodiment, the compounds of the present invention have the formula I:

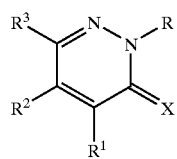

I where

X is selected from the group consisting of O, S, NR$^4$, N—OR$^a$, and N—NR$^b$R$^c$, wherein R$^4$ is selected from the group consisting of alkyl, alkenyl, cycloalkyl, cycloalkenyl, cycloalkylalkyl, cycloalkenylalkyl, aryl, heterocyclic, heterocyclic (alkyl), and arylalkyl; and R$^a$, R$^b$, and R$^c$ are independently selected from the group consisting of alkyl, cycloalkyl, cycloalkylalkyl, aryl, and arylalkyl;

R is selected from the group consisting of hydrogen, alkyl, alkenyl, alkynyl, alkylcarbonylalkyl, alkylsulfonylalkyl, alkylsulfonylarylalkyl, alkoxy, alkoxyalkyl, carboxy, carboxyalkyl, cyanoalkyl, haloalkyl, haloalkenyl, haloalkynyl, hydroxyalkyl, cycloalkyl, cycloalkylalkyl, cycloalkenyl, cycloalkenylalkyl, aryl, arylalkyl, arylalkenyl, arylalkynyl, arylalkoxy, aryloxy, arylcarbonylalkyl, heterocyclic, heterocyclic (alkyl), heterocyclic (alkoxy), heterocyclic (oxy), —C(O)R$^5$, —(CH$_2$)$_n$C(O)R$^5$, —R$^6$—R$^7$, —(CH$_2$)$_n$CH(OH)R$^5$, —(CH$_2$)$_n$CH(OR$^d$)R$^5$, —(CH$_2$)$_n$C(NOR$^d$)R$^5$, —(CH$_2$)$_n$C(NR$^d$)R$^5$, —(CH$_2$)$_n$CH(NOR$^d$)R$^5$, —(CH$_2$)$_n$CH(NR$^d$R$^e$)R$^5$, —(CH$_2$)$_n$C≡C—R$^7$, —(CH$_2$)$_n$[CH(CX'$_3$)]$_m$ —(CH$_2$)$_n$—CX'$_3$, —(CH$_2$)$_n$(C X'$_2$)$_m$—(CH$_2$)$_n$—CX'$_3$, —(CH$_2$)$_n$[CH(CX'$_3$)]$_m$—(CH$_2$)$_n$—R$^8$, —(CH$_2$)$_n$(C X'$_2$)$_m$—(CH$_2$)$_n$R$^8$, —(CH$_2$)$_n$(CHX')$_m$—(CH$_2$)$_n$—CX'$_3$, —(CH$_2$)$_n$(CHX')$_m$—(CH$_2$)$_n$—R$^8$, and —(CH$_2$)$_n$—R$^{20}$, wherein R$^5$ is selected from the group consisting of alkyl, alkenyl, alkynyl, cycloalkyl, cycloalkenyl, aryl, arylalkyl, haloalkyl, haloalkenyl, haloalkynyl, heterocyclic, and heterocyclic (alkyl);

wherein R$^6$ is alkylene or alkenylene;

R$^7$ and R$^8$ are independently selected from the group consisting of hydrogen, alkyl, alkenyl, alkynyl, haloalkyl, cycloalkyl, cycloalkenyl, aryl, arylalkyl, heterocyclic, and heterocyclic (alkyl);

R$^{20}$ is selected from the group consisting of alkyl, alkenyl, haloalkyl, cycloalkyl, cycloalkenyl, aryl, heterocyclic, and heterocyclic (alkyl);

R$^d$ and R$^e$ are independently selected from the group consisting of hydrogen, alkyl, alkenyl, alkynyl, haloalkyl, cycloalkyl, cycloalkenyl, aryl, arylalkyl, heterocyclic, and heterocyclic (alkyl);

X' is halogen;

n is from 0 to about 10, and m is 0 to about 5; at least one of R$^1$, R$^2$ and R$^3$ is a group, substituted with a substituent having a group —X$^1$—R$^9$, having the formula:

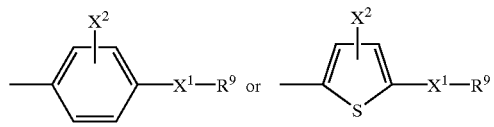

where X$^1$ is selected from the group consisting of —SO$_2$—, —SO(NR$^{10}$)—, —PO(OR$^{11}$)—, and —PO(NR$^{12}$R$^{13}$)—, R$^9$ is selected from the group consisting of alkyl, alkenyl, alkynyl, cycloalkyl, cycloalkenyl, amino, —NHNH$_2$, alkylamino, dialkylamino, alkoxy, thiol, alkylthiol, and protecting groups, X$^2$ is selected from the group consisting of hydrogen or halogen;

R$^{10}$, R$^{11}$, R$^{12}$, and R$^{13}$ are independently selected from the group consisting of hydrogen, alkyl, and cycloalkyl, or R$^{12}$ and R$^{13}$ can be taken together, with the nitrogen to which they are attached, to form a heterocyclic ring having from 3 to 6 atoms.

The remaining two of the groups of $R^1$, $R^2$, and $R^3$, are independently selected from the group consisting of hydrogen, hydroxy, hydroxyalkyl, halogen, alkyl, alkenyl, alkynyl, alkoxy, alkoxyalkyl, amido, amidoalkyl, haloalkyl, cycloalkyl, cycloalkylalkyl, cycloalkenyl, cycloalkenylalkyl, amino, aminocarbonyl, aminocarbonylalkyl, alkylamino, dialkylamino, arylamino, arylalkylamino, diarylamino, aryl, heterocyclic, heterocyclic (alkyl), cyano, nitro, and —Y—$R^{14}$, wherein Y is selected from the group consisting of, —O—, —S—, —C($R^{16}$)($R^{17}$)—, C(O)N$R^{21}$—, —C(O)—, —C(O)O—, —NH—, —NC(O)—, and —N$R^{19}$—. $R^{14}$ is selected from the group consisting of hydrogen, halogen, alkyl, alkenyl, alkynyl, hydroxy, cycloalkyl, cycloalkenyl, amino, cyano, aryl, arylalkyl, heterocyclic, and heterocyclic (alkyl), $R^{16}$, $R^{17}$, and $R^{19}$ are independently selected from the group consisting of alkyl, alkenyl, cycloalkyl, cycloalkenyl, alkoxy, aryl, arylalkyl, heterocyclic, heterocyclic (alkyl), or cyano; and $R^{21}$ is selected from the group consisting of hydrogen, alkyl, alkenyl, cycloalkyl, cycloalkenyl, alkoxy, aryl, arylalkyl, heterocyclic, heterocyclic (alkyl), or cyano; or a pharmaceutically acceptable salt, ester, or prodrug thereof.

In another embodiment, compounds of the present invention have the formula II:

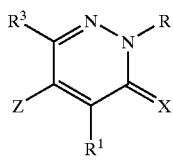

II wherein Z is a group having the formula:

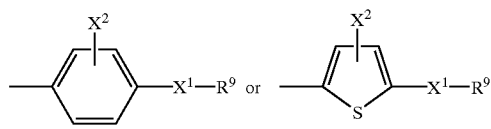

where $X^1$ is selected from the group consisting of —SO$_2$—, -and SO(N$R^{10}$)—, and $R^9$ is selected from the group consisting of alkyl, alkenyl, alkynyl, cycloalkyl, cycloalkenyl, amino, alkylamino, dialkylamino;

$X^2$ is selected from the group consisting of hydrogen or halogen;

X is selected from the group consisting of O, S, N$R^4$, N—O$R^a$, and N—N$R^bR^c$, wherein $R^4$ is selected from the group consisting of alkyl, alkenyl, cycloalkyl, cycloalkenyl, cycloalkylalkyl, cycloalkenylalkyl, aryl, heterocyclic, hetrocyclic (alkyl), and arylalkyl; and $R^a$, $R^b$, and $R^c$ are independently selected from the group consisting of alkyl, cycloalkyl, cycloalkylalkyl, aryl, and arylalkyl;

R is selected from the group consisting of hydrogen, alkyl, alkenyl, alkynyl, alkylcarbonylalkyl, alkylsulfonylalkyl, alkylsulfonylarylalkyl, alkoxy, alkoxyalkyl, carboxy, carboxyalkyl, cyanoalkyl, haloalkyl, haloalkenyl, haloalkynyl, hydroxyalkyl, cycloalkyl, cycloalkylalkyl, cycloalkenyl, cycloalkenylalkyl, aryl, arylalkyl, arylalkenyl, arylalkynyl, arylalkoxy, aryloxy, arylcarbonylalkyl, heterocyclic, heterocyclic (alkyl), heterocyclic (alkoxy), heterocyclic (oxy), —C(O)$R^5$, —(CH$_2$)$_n$C(O)$R^5$, —(CH$_2$)$_n$C≡C—$R^7$, —(CH$_2$)$_n$[CH(CX'$_3$)]$_m$—(CH$_2$)$_n$—CX'$_3$, —(CH$_2$)$_n$(C X'$_2$)$_m$—(CH$_2$)$_n$—CX'$_3$, —(CH$_2$)$_n$[CH(CX'$_3$)]$_m$—(CH$_2$)$_n$—$R^8$, —(CH$_2$)$_n$(C X'$_2$)$_m$—(CH$_2$)$_n$$R^8$, —(CH$_2$)$_n$(CHX')$_m$—(CH$_2$)$_n$—CX'$_3$, —(CH$_2$)$_n$(CHX')$_m$—(CH$_2$)$_n$—$R^8$, and —(CH$_2$)$_n$—$R^{20}$, wherein $R^5$ is selected from the group consisting of alkyl, alkenyl, alkynyl, cycloalkyl, cycloalkenyl, aryl, arylalkyl, haloalkyl, heterocyclic, and heterocyclic (alkyl);

$R^7$ and $R^8$ are independently selected from the group consisting of hydrogen, alkyl, alkenyl, alkynyl, cycloalkyl, cycloalkenyl, aryl, arylalkyl, haloalkyl, heterocyclic, and heterocyclic (alkyl), $R^{20}$ is selected from the group consisting of alkyl, alkenyl, haloalkyl, cycloalkyl, cycloalkenyl, aryl, heterocyclic, and heterocyclic (alkyl);

X' is halogen;

n is from 0 to about 10, m is from 0 to about 5;

$R^1$ and $R^2$ are independently selected from the group consisting of hydrogen, hydroxy, hydroxyalkyl, halogen, alkyl, alkenyl, alkynyl, cycloalkyl, cycloalkylalkyl, cycloalkenyl, cycloalkenylalkyl, amino, alkylamino, dialkylamino, arylamino, arylalkylamino, diarylamino, aryl, heterocyclic, hetreocyclic (alkyl), cyano, nitro, and —Y—$R^{14}$, wherein Y is selected from the group consisting of, —O—, —S—, —CH$_2$—, —C($R^{16}$)($R^{17}$)—, —C(O)—, —C(O)O—, —NH—, and —N$R^{19}$—. $R^{14}$ is selected from the group consisting of hydrogen, halogen, alkyl, alkenyl, alkynyl, hydroxy, cycloalkyl, cycloalkenyl, cyano, aryl, arylalkyl, heterocyclic, and heterocyclic (alkyl), and $R^{16}$, $R^{17}$, and $R^{19}$ are independently selected from the group consisting of alkyl, alkenyl, cycloalkyl, cycloalkenyl, alkoxy, aryl, arylalkyl, hetrocyclic, heterocyclic (alkyl), or cyano;; or a pharmaceutically acceptable salt, ester, or prodrug thereof.

In yet another embodiment, compounds of the present invention have the formula III:

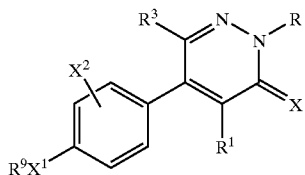

III wherein X, $X^1$, R, $R^1$, $R^3$, and $R^9$ are as defined in Formula I; or a pharmaceutically acceptable salt, ester, or prodrug thereof.

In a preferred embodiment, compounds of the present invention have the formula III, wherein $X^1$ is selected from the group consisting of —SO$_2$—, and —SO(N$R^{10}$)—, and $R^9$ is selected from the group consisting of alkyl, alkenyl, alkynyl, cycloalkyl, cycloalkenyl, amino, alkylamino, or dialkylamino;

X is selected from the group consisting of O, S, N$R^4$, N—O$R^a$, and N—N$R^bR^c$, wherein $R^4$ is selected from the group consisting of alkyl, alkenyl, cycloalkyl, cycloalkenyl, cycloalkylalkyl, cycloalkenylalkyl, aryl, heterocyclic, heterocyclic (alkyl), and arylalkyl; and $R^a$, $R^b$, and $R^c$ are independently selected from the group consisting of alkyl, cycloalkyl, cycloalkylalkyl, aryl, and arylalkyl;

R is selected from the group consisting of hydrogen, alkyl, alkenyl, alkynyl, alkylcarbonylalkyl, alkylsulfonylalkyl, alkylsulfonylarylalkyl, carboxyalkyl, cyanoalkyl, haloalkyl, hydroxyalkyl, cycloalkyl, cycloalkylalkyl, aryl, arylalkenyl, arylalkynyl, heterocyclic, heterocyclic (alkyl), arylalkyl, —$(CH_2)_nC(O)R^5$, —$(CH_2)_nC\equiv C-R^7$, —$(CH_2)_n(CX'_2)_mCX'_3$, —$(CH_2)_n(CX'R^e)_mCX'_3$, —$(CH_2)_n(CX'_2)_mR^8$, —$(CH_2)_n(CH_2)_n(CX'R^e)_mR^8$, and —$(CH_2)_n-R^{20}$;

wherein $R^5$ is selected from the group consisting of alkyl, alkenyl, alkynyl, cycloalkyl, cycloalkenyl, aryl, arylalkyl, haloalkyl, heterocyclic, and heterocyclic (alkyl);

$R^7$ and $R^8$ are independently selected from the group consisting of hydrogen, alkyl, alkenyl, alkynyl, cycloalkyl, cycloalkenyl, aryl, arylalkyl, haloalkyl, heterocyclic, and heterocyclic (alkyl), $R^{20}$ is selected from the group consisting of alkyl, alkenyl, haloalkyl, cycloalkyl, cycloalkenyl, aryl, heterocyclic, and heterocyclic (alkyl);

X' is halogen;

$R^e$ is selected from the group consisting of hydrogen, alkyl, alkenyl, alkynyl, hydroxy, and haloalkyl;

n is from 0 to about 10, m is from 0 to about 5;

$R^1$ and $R^3$ are independently selected from the group consisting of hydrogen, hydroxy, halogen, alkyl, alkenyl, alkynyl, cycloalkyl, cycloalkenyl, amino, alkylamino, dialkylamino, arylamino, arylalkylamino, diarylamino, aryl, heterocyclcic, heterocyclic (alkyl), cyano, and —Y—$R^{14}$, wherein Y is selected from the group consisting of, —O—, —S—, —$CH_2$—, —$CHR^{15}$—, —$C(R^{16})(R^{17})$—, —C(O)—, —NH—, and —$NR^{19}$—. $R^{14}$ is selected from the group consisting of hydrogen, halogen, alkyl, alkenyl, alkynyl, cycloalkyl, cycloalkenyl, cyano, aryl, arylalkyl, heterocyclic, heterocyclic (alkyl), and $R^{15}$, $R^{16}$, $R^{17}$, and $R^{19}$ are independently selected from the group consisting of alkyl, alkenyl, cycloalkyl, cycloalkenyl, alkoxy, aryl, arylalkyl, heterocyclic, heterocyclic (alkyl), or cyano; or a pharmaceutically acceptable salt, ester, or prodrug thereof.

In another preferred embodiment, compounds of the present invention have the formula III, wherein $X^1$ is selected from the group consisting of —$SO_2$—, and —SO($NR^{10}$)—, and $R^9$ is selected from the group consisting of alkyl, alkenyl, alkynyl, cycloalkyl, cycloalkenyl, amino, alkylamino, or dialkylamino;

X is selected from the group consisting of O, S, $NR^4$, N—$OR^a$, and N—$NR^bR^c$, wherein $R^4$ is selected from the group consisting of alkyl, alkenyl, cycloalkyl, cycloalkenyl, alkylcycloalkyl, alkylcycloalkenyl, aryl, heteroaryl, and arylalkyl; and $R^a$, $R^b$, and $R^c$ are independently selected from the group consisting of alkyl, cycloalkyl, alkylcycloalkyl, aryl, and arylalkyl;

R is selected from the group consisting of hydrogen, alkyl, alkenyl, alkynyl, alkylcarbonylalkyl, alkylsulfonylalkyl, alkylsulfonylarylalkyl, carboxyalkyl, cyanoalkyl, haloalkyl, hydroxyalkyl, cycloalkyl, cycloalkylalkyl, aryl, arylalkynyl, heterocyclic, heterocyclic (alkyl), arylalkyl, and —$(CH_2)_nC(O)R^5$,;

wherein $R^5$ is selected from the group consisting of alkyl, alkenyl, alkynyl, cycloalkyl, cycloalkenyl, aryl, arylalkyl, haloalkyl, heterocyclic, and heterocyclic (alkyl); and n is from 0 to about 10;

$R^1$ and $R^3$ are independently selected from the group consisting of hydrogen, aryl, arylalkyl, heterocyclic, heterocyclic (alkyl), and —Y—$R^{14}$, wherein Y is selected from the group consisting of, —O—, —S—, —$CH_2$—, —$CHR^{15}$—, —$C(R^{16})(R^{17})$—, —C(O)—, —NH—, and —$NR^{19}$—. $R^{14}$ is selected from the group consisting of hydrogen, halogen, alkyl, alkenyl, alkynyl, cycloalkyl, cycloalkenyl, cyano, aryl, arylalkyl, heterocyclic, heterocyclic (alkyl), and $R^{15}$, $R^{16}$, $R^{17}$, and $R^{19}$ are independently selected from the group consisting of alkyl, alkenyl, cycloalkyl, cycloalkenyl, alkoxy, aryl, arylalkyl, heterocyclic, heterocyclic (alkyl), or cyano; or a pharmaceutically acceptable salt, ester, or prodrug thereof.

In another preferred embodiment, compounds of the present invention have the formula III, wherein $X^1$ is selected from the group consisting of —SO$_2$—, and —SO(NR$^{10}$)—, and R$^9$ is selected from the group consisting of alkyl, alkenyl, alkynyl, cycloalkyl, cycloalkenyl, amino, alkylamino, or dialkylamino;

X is selected from the group consisting of O, S, NR$^4$, N—OR$^a$, and N—NR$^b$R$^c$, wherein R$^4$ is selected from the group consisting of alkyl, alkenyl, cycloalkyl, cycloalkenyl, alkylcycloalkyl, alkylcycloalkenyl, aryl, heteroaryl, and arylalkyl; and R$^a$, R$^b$, and R$^c$. are independently selected from the group consisting of alkyl, cycloalkyl, alkylcycloalkyl, aryl, and arylalkyl;

R is selected from hydrogen, haloalkyl, aryl, heterocyclic, heterocyclic (alkyl), and —(CH$_2$)$_n$—R$^{20}$ where is R$^{20}$ is substituted and unsubstituted aryl wherein the substituted aryl compounds are substituted with halogen;

n is from 0 to about 10;

R$^1$ and R$^3$ are independently selected from the group consisting of hydrogen, aryl, arylalkyl, heterocyclic, heterocyclic (alkyl), and —Y—R$^{14}$, wherein Y is selected from the group consisting of, —O—, —S—, —CH$_2$—, —CHR$^{15}$—, —C(R$^{16}$) (R$^{17}$)—, —C(O)—, —NH—, and —NR$^{19}$—. R$^{14}$ is selected from the group consisting of hydrogen, halogen, alkyl, alkenyl, alkynyl, cycloalkyl, cycloalkenyl, cyano, aryl, arylalkyl, heterocyclic, heterocyclic (alkyl), and R$^{15}$, R$^{16}$, R$^{17}$, and R$^{19}$ are independently selected from the group consisting of alkyl, alkenyl, cycloalkyl, cycloalkenyl, alkoxy, aryl, arylalkyl, heterocyclic, heterocyclic (alkyl), or cyano; or a pharmaceutically acceptable salt, ester, or prodrug thereof.

In another preferred embodiment, compounds of the present invention have the formula III, wherein X$^1$ is selected from the group consisting of —SO$_2$—, and —SO(NR$^{10}$)—, and R$^9$ is selected from the group consisting of alkyl, alkenyl, alkynyl, cycloalkyl, cycloalkenyl, amino, alkylamino, or dialkylamino;

X is selected from the group consisting of O, S, NR$^4$, N—OR$^a$, and N—NR$^b$R$^c$, wherein R$^4$ is selected from the group consisting of alkyl, alkenyl, cycloalkyl, cycloalkenyl, alkylcycloalkyl, alkylcycloalkenyl, aryl, heteroaryl, and arylalkyl; and R$^a$, R$^b$, and R$^c$. are independently selected from the group consisting of alkyl, cycloalkyl, alkylcycloalkyl, aryl, and arylalkyl;

R is selected from hydrogen, haloalkyl, aryl, heterocyclic, heterocyclic (alkyl), and —(CH$_2$)$_n$—R$^{20}$ where is R$^{20}$ is substituted and unsubstituted aryl wherein the substituted aryl compounds are substituted with halogen;

n is from 0 to about 10;

R$^1$ and R$^3$ are independently selected from the group consisting of hydrogen, aryl, arylalkyl, heterocyclic, and heterocyclic (alkyl); or a pharmaceutically acceptable salt, ester, or prodrug thereof.

In another preferred embodiment, compounds of the present invention have the formula III, wherein X$^1$ is selected from the group consisting of —SO$_2$—, and —SO(NR$^{10}$)—, and R$^9$ is selected from the group consisting of alkyl, alkenyl, alkynyl, cycloalkyl, cycloalkenyl, amino, alkylamino, or dialkylamino;

X is selected from the group consisting of O, S, NR$^4$, N—OR$^a$, and N—NR$^b$R$^c$, wherein R$^4$ is selected from the group consisting of alkyl, alkenyl, cycloalkyl, cycloalkenyl, alkylcycloalkyl, alkylcycloalkenyl, aryl, heteroaryl, and arylalkyl; and R$^a$, R$^b$, and R$^c$ are independently selected from the group consisting of alkyl, cycloalkyl, alkylcycloalkyl, aryl, and arylalkyl;

R is selected from hydrogen, haloalkyl, aryl, heterocyclic, heterocyclic (alkyl), and —(CH$_2$)$_n$—R$^{20}$ where is R$^{20}$ is substituted and unsubstituted aryl wherein the substituted aryl compounds are substituted with halogen;

n is from 0 to about 10;

R$^1$ and R$^3$ are independently selected from the group consisting of hydrogen, phenyl substituted with one, two, or three substituents selected from the group consisting of alkyl, alkoxy, fluorine and chlorine including, but not limited to, p-chlorophenyl, p-fluorophenyl, 3,4-dichlorophenyl, 3-chloro-4-fluorophenyl, and the like; or a pharmaceutically acceptable salt, ester, or prodrug thereof.

In yet another embodiment, compounds of the present invention have formula IV:

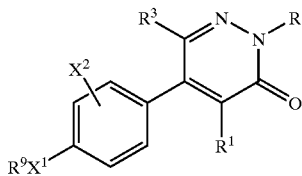

IV where R, R$^1$, X$^1$, X$^2$, R$^9$, and R$^3$ are as described in Formula I; or a pharmaceutically acceptable salt or ester thereof.

In a preferred embodiment, compounds of the present invention have the formula IV, wherein X$^1$ is selected from the group consisting of —SO$_2$—, and —SO(NR$^{10}$)—, and R$^9$ is selected from the group consisting of alkyl, alkenyl, alkynyl, cycloalkyl, cycloalkenyl, amino, alkylamino, or dialkylamino;

R is selected from the group consisting of hydrogen, alkyl, alkenyl, alkynyl, alkylcarbonylalkyl, alkylsulfonylalkyl, alkylsulfonylarylalkyl, carboxyalkyl, cyanoalkyl, haloalkyl, hydroxyalkyl, cycloalkyl, cycloalkylalkyl, aryl, arylalkenyl, arylalkynyl, heterocyclic, heterocyclic (alkyl), arylalkyl, —(CH$_2$)$_n$C(O)R$^5$, —(CH$_2$)$_n$C≡C—R$^7$, —(CH$_2$)$_n$(CX'$_2$)$_m$CX'$_3$, —(CH$_2$)$_n$(CX'R$^e$)$_m$CX'$_3$, —(CH$_2$)$_n$(CX'$_2$)$_m$R$^8$, —(CH$_2$)$_n$(CX'R$^e$)$_m$R$^8$, and —(CH$_2$)$_n$—R$^{20}$;

wherein R$^5$ is selected from the group consisting of alkyl, alkenyl, alkynyl, cycloalkyl, cycloalkenyl, aryl, arylalkyl, haloalkyl, heterocyclic, and heterocyclic (alkyl);

R$^7$ and R$^8$ are independently selected from the group consisting of hydrogen, alkyl, alkenyl, alkynyl, cycloalkyl, cycloalkenyl, aryl, arylalkyl, haloalkyl, heterocyclic, and heterocyclic (alkyl), R$^{20}$ is selected from the group consisting of alkyl, alkenyl, haloalkyl, cycloalkyl, cycloalkenyl, aryl, heterocyclic, and heterocyclic (alkyl);

X' is halogen;

R$^e$ is selected from the group consisting of hydrogen, alkyl, alkenyl, alkynyl, hydroxy, and haloalkyl;

n is from 0 to about 10, m is from 0 to about 5;

R$^1$ is hydrogen and R$^3$ is selected from the group consisting of hydrogen, hydroxy, halogen, alkyl, alkenyl, alkynyl, cycloalkyl, cycloalkenyl, amino, alkylamino, dialkylamino, arylamino, arylalkylamino, diarylamino, aryl, heterocyclcic, heterocyclic (alkyl), cyano, and —Y—R$^{14}$, wherein Y is selected from the group consisting of, —O—, —S—, —CH$_2$—, —CHR$^{15}$—, —C(R$^{16}$)(R$^{17}$)—, —C(O)—, —NH—, and —NR$^{19}$—.

$R^{14}$ is selected from the group consisting of hydrogen, halogen, alkyl, alkenyl, alkynyl, cycloalkyl, cycloalkenyl, cyano, aryl, arylalkyl, heterocyclic, heterocyclic (alkyl), and $R^{15}$, $R^{16}$, $R^{17}$, and $R^{19}$ are independently selected from the group consisting of alkyl, alkenyl, cycloalkyl, cycloalkenyl, alkoxy, aryl, arylalkyl, heterocyclic, heterocyclic (alkyl), or cyano; or a pharmaceutically acceptable salt, ester, or prodrug thereof.

In another preferred embodiment, compounds of the present invention have the formula IV, wherein $X^1$ is selected from the group consisting of —SO$_2$—, and —SO(NR$^{10}$)—, and $R^9$ is selected from the group consisting of alkyl, alkenyl, alkynyl, cycloalkyl, cycloalkenyl, amino, alkylamino, or dialkylamino;

R is selected from the group consisting of hydrogen, alkyl, alkenyl, alkynyl, alkylcarbonylalkyl, alkylsulfonylalkyl, alkylsulfonylarylalkyl, carboxyalkyl, cyanoalkyl, haloalkyl, hydroxyalkyl, cycloalkyl, cycloalkylalkyl, aryl, arylalkenyl, arylalkynyl, heterocyclic, heterocyclic (alkyl), arylalkyl, —(CH$_2$)$_n$C(O)R$^5$ and —(CH$_2$)$_n$—R$^{20}$;

wherein $R^5$ is selected from the group consisting of alkyl, alkenyl, alkynyl, cycloalkyl, cycloalkenyl, aryl, arylalkyl, haloalkyl, heterocyclic, and heterocyclic (alkyl);

$R^{20}$ is selected from the group consisting of alkyl, alkenyl, haloalkyl, cycloalkyl, cycloalkenyl, aryl, heterocyclic, and heterocyclic (alkyl);

n is from 0 to about 10;

$R^1$ is hydrogen and $R^3$ is selected from the group consisting of hydrogen, hydroxy, halogen, alkyl, alkenyl, alkynyl, cycloalkyl, cycloalkenyl, amino, alkylamino, dialkylamino, arylamino, arylalkylamino, diarylamino, aryl, heterocyclcic, heterocyclic (alkyl), cyano, and —Y—R$^{14}$, wherein Y is selected from the group consisting of, —O—, —S—, —CH$_2$—, —CHR$^{15}$—, —C(R$^{16}$)(R$^{17}$)—, —C(O)—, —NH—, and —NR$^{19}$—. $R^{14}$ is selected from the group consisting of hydrogen, halogen, alkyl, alkenyl, alkynyl, cycloalkyl, cycloalkenyl, cyano, aryl, arylalkyl, heterocyclic, heterocyclic (alkyl), and $R^{15}$, $R^{16}$, $R^{17}$, and $R^{19}$ are independently selected from the group consisting of alkyl, alkenyl, cycloalkyl, cycloalkenyl, alkoxy, aryl, arylalkyl, heterocyclic, heterocyclic (alkyl), or cyano; or a pharmaceutically acceptable salt, ester, or prodrug thereof.

In another preferred embodiment, compounds of the present invention have the formula IV, wherein $X^1$ is selected from the group consisting of —SO$_2$—, and —SO(NR$^{10}$)—, and $R^9$ is selected from the group consisting of alkyl, alkenyl, alkynyl, cycloalkyl, cycloalkenyl, amino, alkylamino, or dialkylamino;

R is selected from the group consisting of hydrogen, alkyl, alkenyl, alkynyl, alkylcarbonylalkyl, alkylsulfonylalkyl, alkylsulfonylarylalkyl, carboxyalkyl, cyanoalkyl, haloalkyl, hydroxyalkyl, cycloalkyl, cycloalkylalkyl, aryl, arylalkynyl, heterocyclic, heterocyclic (alkyl), arylalkyl, and —(CH$_2$)$_n$C(O)R$^5$;

wherein $R^5$ is selected from the group consisting of alkyl, alkenyl, alkynyl, cycloalkyl, cycloalkenyl, aryl, arylalkyl, haloalkyl, heterocyclic, and heterocyclic (alkyl); and n is from 0 to about 10;

$R^1$ is hydrogen and $R^3$ is selected from the group consisting of hydrogen, aryl, arylalkyl, heterocyclic, heterocyclic (alkyl), and —Y—R$^{14}$, wherein Y is selected from the group consisting of, —O—, —S—, —CH$_2$—, —CHR$^{15}$—, —C(R$^{16}$)(R$^{17}$)—, —C(O)—, —NH—, and —NR$^{19}$—. $R^{14}$ is selected from the group consisting of hydrogen, halogen, alkyl, alkenyl, alkynyl, cycloalkyl, cycloalkenyl, cyano, aryl, arylalkyl, heterocyclic, heterocyclic (alkyl), and $R^{15}$, $R^{16}$, $R^{17}$, and $R^{19}$ are independently selected from the group consisting of alkyl, alkenyl, cycloalkyl, cycloalkenyl, alkoxy, aryl, arylalkyl, heterocyclic, heterocyclic (alkyl), or cyano; or a pharmaceutically acceptable salt, ester, or prodrug thereof.

In another preferred embodiment, compounds of the present invention have the formula IV, wherein $X^1$ is selected from the group consisting of —SO$_2$—, and —SO(NR$^{10}$)—, and $R^9$ is selected from the group consisting of alkyl, alkenyl, alkynyl, cycloalkyl, cycloalkenyl, amino, alkylamino, or dialkylamino;

R is selected from hydrogen, haloalkyl, aryl, heterocyclic, heterocyclic (alkyl), and —(CH$_2$)$_n$—R$^{20}$ where is $R^{20}$ is substituted and unsubstituted aryl wherein the substituted aryl compounds are substituted with halogen;

n is from 0 to about 10;

$R^1$ is hydrogen and $R^3$ is selected from the group consisting of hydrogen, aryl, arylalkyl, heterocyclic, heterocyclic (alkyl), and —Y—R$^{14}$, wherein Y is selected from the group consisting of, —O—, —S—, —CH$_2$—, —CHR$^{15}$—, —C(R$^{16}$)(R$^{17}$)—, —C(O)—, —NH—, and —NR$^{19}$—. $R^{14}$ is selected from the group consisting of hydrogen, halogen, alkyl, alkenyl, alkynyl, cycloalkyl, cycloalkenyl, cyano, aryl, arylalkyl, heterocyclic, heterocyclic (alkyl), and $R^{15}$, $R^{16}$, $R^{17}$, and $R^{19}$ are independently selected from the group consisting of alkyl, alkenyl, cycloalkyl, cycloalkenyl, alkoxy, aryl, arylalkyl, heterocyclic, heterocyclic (alkyl), or cyano.

In another preferred embodiment, compounds of the present invention have the formula IV, wherein $X^1$ is selected from the group consisting of —SO$_2$—, and —SO(NR$^{10}$)—, and $R^9$ is selected from the group consisting of alkyl, alkenyl, alkynyl, cycloalkyl, cycloalkenyl, amino, alkylamino, or dialkylamino;

R is selected from hydrogen, haloalkyl, aryl, heterocyclic, heterocyclic (alkyl), and —(CH$_2$)$_n$—R$^{20}$ where is $R^{20}$ is substituted and unsubstituted aryl wherein the substituted aryl compounds are substituted with halogen;

n is from 0 to about 10;

$R^1$ is hydrogen and $R^3$ is selected from the group consisting of hydrogen, aryl, arylalkyl, heterocyclic, and heterocyclic (alkyl); or a pharmaceutically acceptable salt, ester, or prodrug thereof.

In another preferred embodiment, compounds of the present invention have the formula IV, wherein $X^1$ is selected from the group consisting of —SO$_2$—, and —SO(NR$^{10}$)—, and $R^9$ is selected from the group consisting of alkyl, alkenyl, alkynyl, cycloalkyl, cycloalkenyl, amino, alkylamino, or dialkylamino;

R is selected from hydrogen, haloalkyl, aryl, heterocyclic, heterocyclic (alkyl), and —(CH$_2$)$_n$—R$^{20}$ where is $R^{20}$ is substituted and unsubstituted aryl wherein the substituted aryl compounds are substituted with halogen;

n is from 0 to about 10;

$R^1$ is hydrogen and $R^3$ is selected from the group consisting of hydrogen, phenyl substituted with one, two, or three substituents selected from the group consisting of alkyl, alkoxy, fluorine and chlorine including, but not limited to, p-chlorophenyl, p-fluorophenyl, 3,4-dichlorophenyl, 3-chloro-4-fluoro-phenyl, and the like; or a pharmaceutically acceptable salt, ester, or prodrug thereof.

In another preferred embodiment, compounds of the present invention have the formula IV, wherein $X^1$ is selected from the group consisting of —$SO_2$—, and —SO($NR^{10}$)—, and $R^9$ is selected from the group consisting of alkyl, alkenyl, alkynyl, cycloalkyl, cycloalkenyl, amino, alkylamino, or dialkylamino;

R is haloalkyl, $R^1$ is hydrogen and $R^3$ is selected from the group consisting of hydrogen and phenyl substituted with one, two, or three substituents selected from the group consisting of alkyl, alkoxy, fluorine and chlorine; or a pharmaceutically acceptable salt, ester, or prodrug thereof.

In another preferred embodiment, compounds of the present invention have the formula IV, wherein $X^1$ is selected from the group consisting of —$SO_2$—, and —SO($NR^{10}$)—, and $R^9$ is selected from the group consisting of alkyl, alkenyl, alkynyl, cycloalkyl, cycloalkenyl, amino, alkylamino, or dialkylamino;

R is substituted and unsubstituted aryl and $R^1$ is hydrogen and $R^3$ is selected from the group consisting of hydrogen and phenyl substituted with one, two, or three substituents selected from the group consisting of alkyl, alkoxy, fluorine and chlorine; or a pharmaceutically acceptable salt, ester, or prodrug thereof.

In another preferred embodiment, compounds of the present invention have the formula IV, wherein X' is $SO_2$, $R^9$ is selected from alkyl and amino, R is substituted and unsubstituted aryl and $R^1$ is hydrogen and $R^3$ is selected from the group consisting of hydrogen and phenyl substituted with one, two, or three substituents selected from the group consisting of alkyl, alkoxy, fluorine and chlorine; or a pharmaceutically acceptable salt, ester, or prodrug thereof.

Preferred Embodiments

Compounds useful in practicing the present invention include, but are not limited to:

5-(4-Methylsulfonylphenyl)-6-(4-fluorophenyl)-3(2H)-pyridazinone;
2-Benzyl-5-(4-methylsulfonylphenyl)-6-(4-fluorophenyl)-3(2H)-pyridazinone;
2-Methyl-5-(4-methylsulfonylphenyl)-6-(4-fluorophenyl)-3(2H)-pyridazinone;
2-Ethyl-5-(4-methylsulfonylphenyl)-6-(4-fluorophenyl)-3(2H)-pyridazinone;
2-(4-Fluorobenzyl)-5-(4-methylsulfonylphenyl)-6-(4-fluorophenyl)-3(2H)-pyridazinone;
2-(n-Butyl)-5-(4-methylsulfonylphenyl)-6-(4-fluorophenyl)-3(2H)-pyridazinone;
2-(2,2,2-Trifluroethyl)-5-(4-methylsulfonylphenyl)-6-(4-flurophenyl)-3(2H)-pyridazinone;
2-(4-Fluoro-α-methylbenzyl)-5-(4-methylsulfonylphenyl)-6-(4-fluorophenyl)-3(2H)-pyridazinone;
2-(n-Propyl)-5-(4-methylsulfonylphenyl)-6-(4-fluorophenyl)-3(2 H)-pyridazinone;
2-(n-Pentyl)-5-(4-methylsulfonylphenyl)-6-(4-fluorophenyl)-3(2 H)-pyridazinone;
2-Cyclohexylmethyl-5-(4-methylsulfonylphenyl)-6-(4-fluorophenyl)-3(2 H)-pyridazinone;
2-Phenacyl-5-(4-methylsulfonylphenyl)-6-(4-fluorophenyl)-3(2 H)-pyridazinone;
2-Propargyl-5-(4-methylsulfonylphenyl)-6-(4-fluorophenyl)-3(2H)-pyridazinone;
2-Cyclohexyl-5-(4-methylsulfonylphenyl)-6-(4-fluorophenyl)-3(2H)-pyridazinone;
2-(2-Butynyl)-5-(4-methylsulfonylphenyl)-6-(4-fluorophenyl)-3(2H)-pyridazinone;
2-(Cyclobutanylmethyl)-5-(4-methylsulfonylphenyl)-6-(4-fluorophenyl)-3(2H)-pyridazinone; and
2-(3-Methylbuten-2-yl)-5-(4-methylsulfonylphenyl)-6-(4-fluorophenyl)-3(2H)-pyridazinone; or a pharmaceutically acceptable salt, ester, or prodrug thereof.

Preparation of Compounds of the Invention

The compounds of the invention may be prepared by a variety of synthetic routes. Representative procedures are outlined in Scheme 1 below. A general route to the compounds of the invention having Formula III, where the aryl group at the 5-position on the pyridazinone ring is substituted with a sulfonyl group ring ($R^2$ is aminosulfonyl, or methylsulfonyl, shown as methylsulfonyl) is described in Scheme 1, below. Phenyl acetic acid, optionally substituted, was condensed with a benzaldehyde to form the corresponding 2-phenyl-trans-cinnamic acid. The trans-cinnamic acid was converted to the corresponding acid chloride which was then decarbonylated to provide the benzyl-aryl ketone. The ketone was then alkylated with ethyl bromoacetate in the presence of a strong base such as sodium bis(trimethylsilyl) amide. Treatment of the ketoester product with hydrazine, in an alcohol solvent, such as ethanol, provided dihydropyridazinone. The dihydropyridazinone was dehydrogenated to form the pyridazinone by treatment with Bromine in acetic acid. If desired, the R' group can be added via substitution using an appropriate alkylating agent. In Scheme 1, X is defined as in $R^3$ and R' is defined as in R.

SCHEME 1

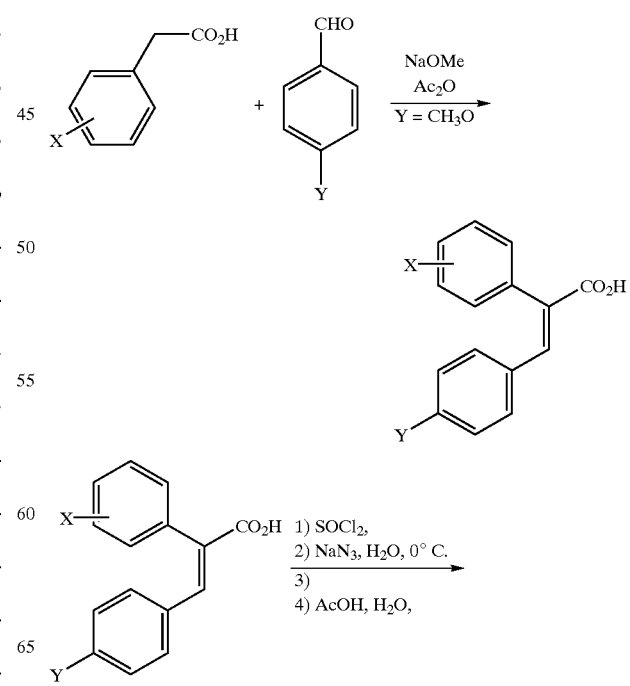

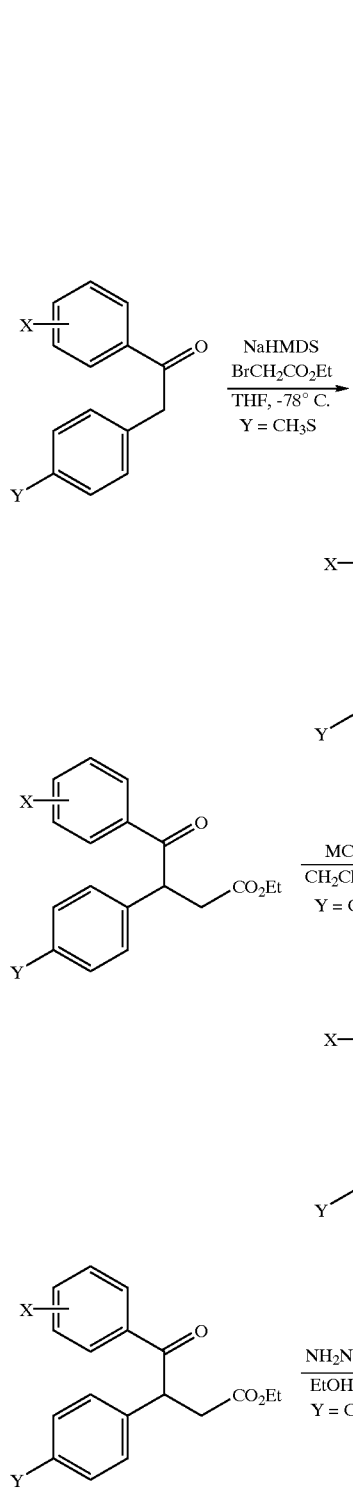
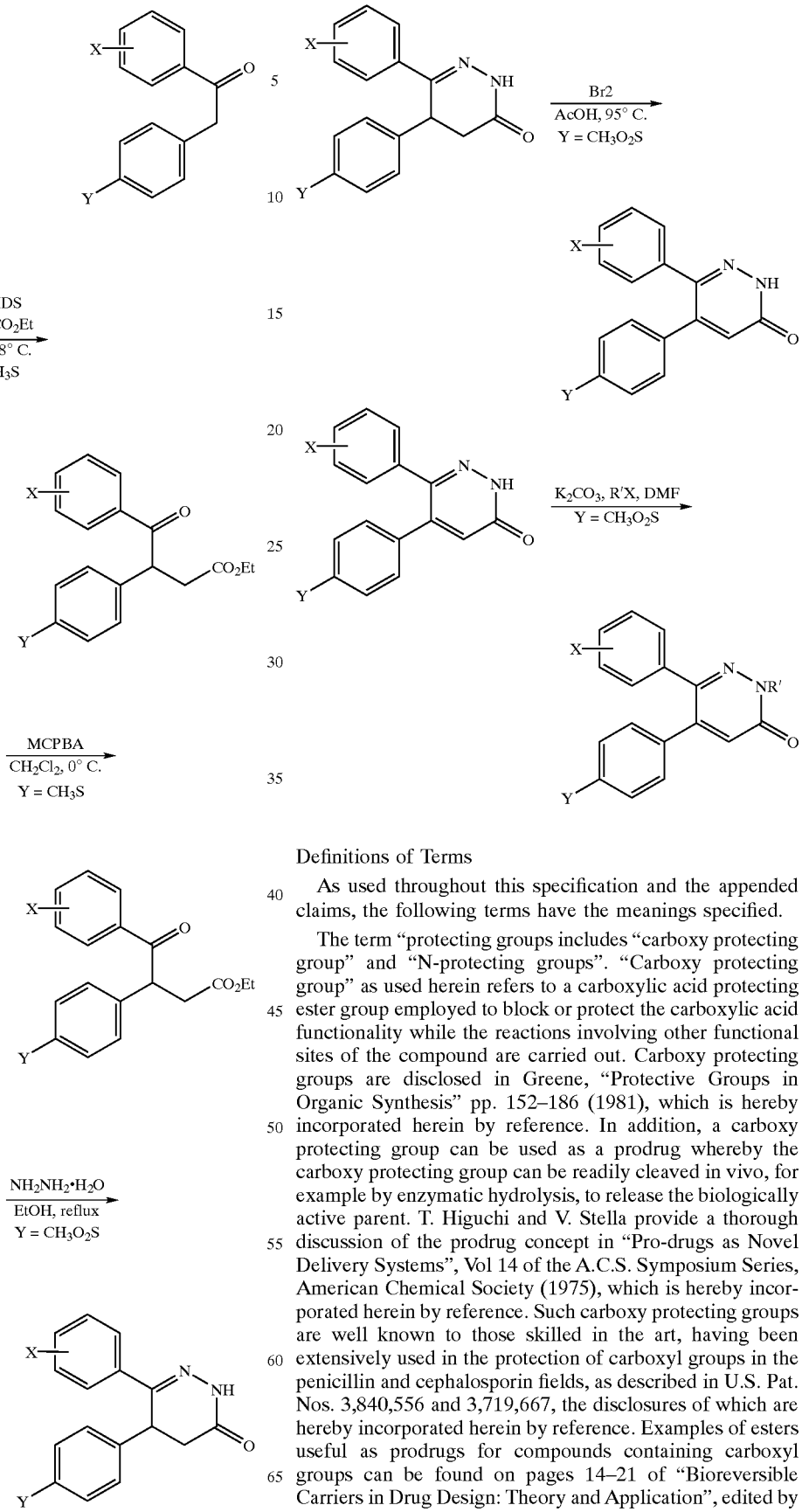

Definitions of Terms

As used throughout this specification and the appended claims, the following terms have the meanings specified.

The term "protecting groups includes "carboxy protecting group" and "N-protecting groups". "Carboxy protecting group" as used herein refers to a carboxylic acid ester group employed to block or protect the carboxylic acid functionality while the reactions involving other functional sites of the compound are carried out. Carboxy protecting groups are disclosed in Greene, "Protective Groups in Organic Synthesis" pp. 152–186 (1981), which is hereby incorporated herein by reference. In addition, a carboxy protecting group can be used as a prodrug whereby the carboxy protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy protecting groups are well known to those skilled in the art, having been extensively used in the protection of carboxyl groups in the penicillin and cephalosporin fields, as described in U.S. Pat. Nos. 3,840,556 and 3,719,667, the disclosures of which are hereby incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy protecting groups are $C_1$ to $C_8$ alkyl (e.g., methyl, ethyl or tertiary butyl and the like); haloalkyl; alkenyl; cycloalkyl and substituted derivatives thereof such as cyclohexyl, cylcopentyl and the like; cycloalkylalkyl and substituted derivatives thereof such as cyclohexylmethyl, cylcopentylmethyl and the like; arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (t-Boc) and benzyloxycarbonyl (Cbz).

The term "alkanoyl" as used herein refers to an alkyl group as previously defined appended to the parent molecular moiety through a carbonyl (—C(O)—) group. Examples of alkanoyl include acetyl, propionyl and the like.

The term "alkanoylamino" as used herein refers to an alkanoyl group as previously defined appended to an amino group. Examples alkanoylamino include acetamido, propionylamido and the like.

The term "alkenyl" as used herein refers to a straight or branched chain hydrocarbon radical containing from 2 to 15 carbon atoms and also containing at least one carbon-carbon double bond. Alkenyl groups include, for example, vinyl (ethenyl), allyl (propenyl), butenyl, 1-methyl-2-buten-1-yl and the like.

The term "alkenylene" denotes a divalent group derived from a straight or branched chain hydrocarbon containing from 2 to 15 carbon atoms and also containing at least one carbon-carbon double bond. Examples of alkenylene include —CH=CH—, —CH₂CH=CH—, —C(CH₃)=CH—, —CH₂CH=CHCH₂—, —CH₂CH=CHCH₂CH=CHCH₂—, and the like.

The term "alkenyloxy" as used herein refers to an alkenyl group, as previously defined, connected to the parent molecular moiety through an oxygen (—O—) linkage. Examples of alkenyloxy include allyloxy, butenyloxy and the like.

The term "alkoxy" as used herein refers to $R_{41}O$— wherein $R_{41}$ is a loweralkyl group, as defined herein. Examples of alkoxy include, but are not limited to, ethoxy, tert-butoxy, and the like.

The term "alkoxyalkoxy" as used herein refers to $R_{80}O$—$R_{81}O$— wherein $R_{80}$ is loweralkyl as defined above and $R_{81}$ is alkylene. Representative examples of alkoxyalkoxy groups include methoxymethoxy, ethoxymethoxy, t-butoxymethoxy and the like.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, isopropoxycarbonyl and the like.

The term "alkoxyalkoxyalkenyl" as used herein refers to an alkoxyalkoxy group as previously defined appended to an alkenyl radical. Representative examples of alkoxyalkoxyalkenyl groups include methoxyethoxyethenyl, methoxymethoxymethenyl, and the like.

The term "alkoxyalkyl" as used herein refers to an alkoxy group as previously defined appended to an alkylene as previously defined. Examples of alkoxyalkyl include, but are not limited to, methoxymethyl, methoxyethyl, isopropoxymethyl and the like.

The term "(alkoxycarbonyl)thioalkoxy" as used herein refers to an alkoxycarbonyl group as previously defined appended to a thioalkoxy radical. Examples of (alkoxycarbonyl)thioalkoxy include methoxycarbonylthiomethoxy, ethoxycarbonylthiomethoxy and the like.

The terms "alkyl" and "loweralkyl" as used herein refer to straight or branched chain alkyl radicals containing from 1 to 15 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkylamino" as used herein refers to $R_{51}NH-$ wherein $R_{51}$ is a loweralkyl group, for example, ethylamino, butylamino, and the like.

The term "alkylcarbonylalkyl" as used herein refers to $R_{40}-C(O)-R_{41}-$ wherein $R_{40}$ is an alkyl group and $R_{41}$ is alkylene.

The term "alkylene" denotes a divalent group derived from a straight or branched chain saturated hydrocarbon having from 1 to 15 carbon atoms by the removal of two hydrogen atoms, for example $-CH_2-$, $-CH_2CH_2-$, $-CH(CH_3)-$, $-CH_2CH_2CH_2-$, $-CH_2C(CH_3)_2CH_2-$ and the like.

The term "alkylsulfonyl" as used herein refers to an alkyl group as previously defined appended to the parent molecular moiety through a sulfonyl ($-S(O)_2-$) group. Examples of alkylsulfonyl include methylsulfonyl, ethylsulfonyl, isopropylsulfonyl and the like.

The term "alkylsulfonylalkyl" as used herein refers to an alkyl group as previously defined appended to the parent molecular moiety through a sulfonylalkyl ($-S(O)_2-R_{52}-$) group wherein $R_{52}$ is alkylene. Examples of alkylsulfonylalkyl include methylsulfonylmethyl ($CH_3-S(O)_2-CH_2-$), ethylsulfonylmethyl, isopropylsulfonylethyl and the like.

The term "alkylsulfonylamino" as used herein refers to an alkyl group as previously defined appended to the parent molecular moiety through a sulfonylamino ($-S(O)_2-NH-$) group. Examples of alkylsulfonylamino include methylsulfonylamino, ethylsulfonylamino, isopropylsulfonylamino and the like.

The term "alkylsulfonylarylalkyl" as used herein refers to an alkyl group as previously defined appended to the parent molecular moiety through a sulfonylalkyl ($-S(O)_2-R_{45}R_{33}-$) group wherein $R_{45}$ is aryl and $R_{33}$ is alkylene. Examples of alkylsulfonylarylalkyl include methylsulfonylphenylmethyl ethylsulfonylphenylmethyl, isopropylsulfonylphenylethyl and the like.

The term "alkylthio" as used herein refers to $R_{53}S-$ wherein $R_{53}$ is alkyl.

The term "alkynyl" as used herein refers to a straight or branched chain hydrocarbon radical containing from 2 to 15 carbon atoms and also containing at least one carbon-carbon triple bond. Examples of alkynyl include $-C\equiv-C-H$, $H-C\equiv C-CH_2-$, $H-C\equiv C-CH(CH_3)-$ and the like.

The term "amido" as used herein refers to $R_{54}-C(O)-NH-$ wherein $R_{54}$ is an alkyl group.

The term "amidoalkyl" as used herein refers to $R_{34}-C(O)-NHR_{35}-$ wherein $R_{34}$ is alkyl and $R_{35}$ is alkylene.

The term "amino" as used herein refers $-NH_2$.

The term "aminocarbonyl" as used herein refers to $H_2N-C(O)-$.

The term "aminocarbonylalkyl" as used herein refers to an aminocarbonyl as described above appended to the parent molecular moiety through an alkylene.

The term "aminocarbonylalkoxy" as used herein refers to $H_2N-C(O)-O-R_{55}-$, wherein $R_{55}$ is an alkyl radical group. Examples of aminocarbonylalkoxy include aminocarbonylmethoxy, aminocarbonylethoxy and the like.

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups can be unsubstituted or substituted with one, two or three substituents independently selected from loweralkyl, halo, haloalkyl, haloalkoxy, hydroxy, oxo (=O), hydroxyalkyl, alkenyloxy, alkoxy, alkoxyalkoxy, alkoxycarbonyl, alkoxycarbonylalkenyl, (alkoxycarbonyl)thioalkoxy, thioalkoxy, alkylimino (R*N= wherein R* is a loweralkyl group), amino, alkylamino, alkylsulfonyl, dialkylamino, aminocarbonyl, aminocarbonylalkoxy, alkanoylamino, aryl, arylalkyl, arylalkoxy, aryloxy, mercapto, cyano, nitro, mercapto, carboxy, carboxaldehyde, carboxamide, cycloalkyl, carboxyalkenyl, carboxyalkoxy, alkylsulfonylamino, cyanoalkoxy, (heterocyclic)alkoxy, $-SO_3H$, hydroxalkoxy, phenyl and tetrazolylalkoxy. Examples of substituted aryl include 3-chlorophenyl, 3-fluorophenyl, 4-chlorophenyl, 4-fluorophenyl, 3,4-dichlorophenyl, 3-chloro-4-fluoro-phenyl, 4-methylsulfonylphenyl, and the like.

The term "arylalkenyl" as used herein refers to an alkenylene to which is appended an aryl group, for example, phenylethenyl and the like.

The term "arylalkynyl" as used herein refers to an alkynyl radical to which is appended an aryl group, for example, phenylethynyl and the like The term "arylalkoxy" as used herein refers to $R_{42}O-$ wherein $R_{42}$ is an arylalkyl group, for example, benzyloxy, and the like.

The term "arylalkyl" as used herein refers to an aryl group as previously defined, appended to a loweralkyl radical, for example, benzyl and the like.

The term "arylalkylamino" as used herein refers to an arylalkyl group as previously defined, appended to the parent molecular moiety through an amino group.

The term "arylamino" as used herein refers to $R_{45}NH_2-$ wherein $R_{45}$ is an aryl.

The term "arylcarbonylalkyl" as used herein refers to $R_{45}C(O)R_{33}-$ wherein $R_{45}$ is an aryl group and $R_{33}$ is an alkylene group.

The term "aryloxy" as used herein refers to $R_{45}O-$ wherein $R_{45}$ is an aryl group, for example, phenoxy, and the like.

The term "carboxaldehyde" as used herein refers to a formaldehyde radical, $-C(O)H$.

The term "carboxamide" as used herein refers to $-C(O)NH_2$.

The term "carboxy" as used herein refers to a carboxylic acid radical, $-C(O)OH$.

The term "carboxyalkenyl" as used herein refers to a carboxy group as previously defined appended to an alkenyl radical as previously defined. Examples of carboxyalkenyl include 2-carboxyethenyl, 3-carboxy-1-ethenyl and the like.

The term "carboxyalkyl" as used herein refers to a carboxy group as previously defined appended to an alkyl radical as previously defined. Examples of carboxyalkyl include 2-carboxyethyl, 3-carboxy-1-propyl and the like.

The term "carboxyalkoxy" as used herein refers to a carboxy group as previously defined appended to an alkoxy radical as previously defined. Examples of carboxyalkoxy include carboxymethoxy, carboxyethoxy and the like.

The term "cyano" as used herein refers a cyano ($-CN$) group.

The term "cyanoalky" as used herein refers to a cyano ($-CN$) group appended to the parent molecular moiety through an alkyl. Examples of cyanoalkyl include 3-cyanopropyl, 4-cyanobutyl, and the like.

The term "cyanoalkoxy" as used herein refers to a cyano (—CN) group appended to the parent molecular moiety through an alkoxy radical. Examples of cyanoalkoxy include 3-cyanopropoxy, 4-cyanobutoxy and the like.

The term "cycloalkyl" as used herein refers to an aliphatic ring system having 3 to 10 carbon atoms and 1 to 3 rings including, but not limited to, cyclopropyl, cyclopentyl, cyclohexyl, and the like. Cycloalkyl groups can be unsubstituted or substituted with one, two or three substituents independently selected from hydroxy, halo, oxo (=O), alkylimino (R*N= wherein R* is a loweralkyl group), amino, alkylamino, dialkylamino, alkoxy, alkoxyalkoxy, alkoxycarbonyl, thioalkoxy, haloalkyl, mercapto, carboxy, carboxaldehyde, carboxamide, cycloalkyl, aryl, arylalkyl, —SO₃H, nitro, cyano and loweralkyl.

The term "cycloalkenyl" as used herein refers to an aliphatic ring system having 3 to 10 carbon atoms and 1 to 3 rings containing at least one double bond in the ring structure. Cycloalkenyl groups can be unsubstituted or substituted with one, two or three substituents independently selected hydroxy, halo, oxo (=O), alkylimino (R*N= wherein R* is a loweralkyl group), amino, alkylamino, dialkylamino, alkoxy, alkoxyalkoxy, alkoxycarbonyl, thioalkoxy, haloalkyl, mercapto, carboxy, carboxaldehyde, carboxamide, cycloalkyl, aryl, arylalkyl, —SO₃H, nitro, cyano and loweralkyl.

The term "cycloalkylalkyl" as used herein refers to a cycloalkyl group appended to a loweralkyl radical, including but not limited to cyclohexylmethyl.

The term "cycloalkenylalkyl" as used herein refers to a cycloalkenyl group appended to a loweralkyl radical, including but not limited to cyclohexenylmethyl.

The term "dialkylamino" as used herein refers to $(R_{56})(R_{57})N-$ wherein $R_{56}$ and $R_{57}$ are independently selected from loweralkyl, for example diethylamino, methyl propylamino, and the like.

The term "diarylamino" as used herein refers to $(R_{45})(R_{46})N-$ wherein $R_{45}$ and $R_{46}$ are independently aryl, for example diphenylamino and the like.

The term "halo" or "halogen" as used herein refers to I, Br, Cl or F.

The term "haloalkyl" as used herein refers to an alkyl radical, as defined above, which has at least one halogen substituent, for example, chloromethyl, fluoroethyl, trifluoromethyl or pentafluoroethyl, 2,3-difluoropentyl, and the like.

The term "haloalkenyl" as used herein refers to an alkenyl radical has at least one halogen substituent.

The term "haloalkynyl" as used herein refers to an alkynyl radical has at least one halogen substituent.

The term "haloalkoxy" as used herein refers to an alkoxy radical as defined above, bearing at least one halogen substituent, for example, 2-fluoroethoxy, 2,2,2-trifluoroethoxy, trifluoromethoxy, 2,2,3,3,3-pentafluoropropoxy and the like.

The term "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; or two sulfur atoms in non-adjacent positions. Examples of heterocycles include, but are not limited to, thiophene, pyrrole, and furan. The 5-membered ring has 0–2 double bonds and the 6- and 7-membered rings have 0–3 double bonds. The nitrogen heteroatoms can be optionally quaternized. The term "heterocyclic" also includes bicyclic groups in which any of the above heterocyclic rings is fused to a benzene ring or a cycloalkane ring or another heterocyclic ring (for example, indolyl, dihydroindolyl, quinolyl, isoquinolyl, tetrahydroquinolyl, tetrahydroisoquinolyl, decahydroquinolyl, decahydroisoquinolyl, benzofuryl, dihydrobenzofuryl or benzothienyl and the like). Heterocyclics include: aziridinyl, azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, oxetanyl, furyl, tetrahydrofuranyl, thienyl, thiazolidinyl, isothiazolyl, triazolyl, tetrazolyl, isoxazolyl, oxadiazolyl, thiadiazolyl, pyrrolyl pyrimidyl and benzothienyl. Heterocyclics also include compounds of the formula

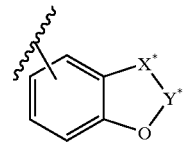

where X* is —CH₂— or —O— and Y* is —C(O)— or [—C(R")₂—]ᵥ where R" is hydrogen or $C_1$–$C_4$-alkyl and v is 1, 2 or 3 such as 1,3-benzodioxolyl, 1,4-benzodioxanyl and the like. Heterocyclics also include bicyclic rings such as quinuclidinyl and the like.

Heterocyclics can be unsubstituted or be substituted with one, two, or three substituents independently selected from hydroxy, halo, oxo (=O), alkylimino (R*N= wherein R* is a loweralkyl group), amino, alkylamino, dialkylamino, alkoxy, alkoxyalkoxy, alkoxycarbonyl, thioalkoxy, haloalkyl, mercapto, carboxy, carboxaldehyde, carboxamide, cycloalkyl, aryl, arylalkyl, —SO₃H, nitro, cyano and loweralkyl. In addition, nitrogen containing heterocycles can be N-protected.

The term "heterocyclic(alkoxy)" as used herein refers to a heterocyclic group as defined above appended to an alkoxy radical as defined above. Examples of (heterocyclic)alkoxy include 4-pyridylmethoxy, 2-pyridylmethoxy and the like.

The term "heterocyclic(alkyl)" as used herein refers to a heterocyclic group as defined above appended to the parent molecular moiety through a loweralkyl radical as defined above.

The term "heterocyclic(oxy)" as used herein refers to a heterocyclic group as defined above appended to the parent molecular moiety through an oxygen. Examples of (heterocyclic)oxy include 4-pyridyloxy, 2-pyridyloxy and the like.

The term "hydroxy" as used herein refers to —OH.

The term "hydroxyalkoxy" as used herein refers to an alkoxy radical as previously defined to which is appended a hydroxy (—OH) group. Examples of hydroxyalkoxy include 3-hydroxypropoxy, 4-hydroxybutoxy and the like.

The term "hydroxyalkyl" as used herein refers to a loweralkyl radical to which is appended a hydroxy group.

The term "mercapto" or "thiol" as used herein refers to —SH.

The term "nitro" as used herein refers to —NO₂.

The term "thioalkoxy" as used herein refers to $R_{70}S$— wherein $R_{70}$ is alkoxy. Examples of thioalkoxy include, but are not limited to, methylthio, ethylthio and the like.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid.

Basic addition salts can be prepared in situ during the final isolation and purification of the compounds of formula (I), or separately by reacting a carboxylic acid function with a suitable base such as the hydroxide, carbonate or bicarbonate of a pharmaceutically acceptable metal cation or with ammonia, or an organic primary, secondary or tertiary amine. Such pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The term "pharmaceutically acceptable ester" as used herein refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyates, acrylates and ethylsuccinates.

The term "pharmaceutically acceptable prodrug" as used herein refers to those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to provide the parent compound having the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

As used throughout this specification and the appended claims, the term metabolically cleavable group denotes a moiety which is readily cleaved in vivo from the compound bearing it, wherein said compound, after cleavage remains or becomes pharmacologically active. Metabolically cleavable groups form a class of groups reactive with the carboxyl group of the compounds of this invention are well known to practitioners of the art. They include, but are not limited to groups such as, for example, alkanoyl, such as acetyl, propionyl, butyryl, and the like; unsubstituted and substituted aroyl, such as benzoyl and substituted benzoyl; alkoxycarbonyl, such as ethoxycarbonyl; trialkylsilyl, such as trimethyl- and triethysilyl; monoesters formed with dicarboxylic acids, such as succinyl, and the like. Because of the ease with which the metabolically cleavable groups of the compounds of this invention are cleaved in vivo, the compounds bearing such groups act as pro-drugs of other prostaglandin biosynthesis inhibitors. The compounds bearing the metabolically cleavable groups have the advantage that they may exhibit improved bioavailability as a result of enhanced solubility and/or rate of absorption conferred upon the parent compound by virtue of the presence of the metabolically cleavable group.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts.

The following examples illustrate the process of the invention, without limitation.

EXAMPLE 1

2-(4-Fluorophenyl)-4-methylthio-trans-cinnamic acid

To a stirred solution of 4-fluorophenylacetic acid (48.8 g, 0.31 mol.) and 4-(methylthio)benzaldehyde (50 g, 0.31 mol.) in acetic anhydride (50 mL) was added sodium methoxide (18.8 g, 0.33 mol.). The solution was stirred at reflux for 18 hours. The reaction mixture was allowed to cool to room temperature and a yellow precipitate formed. The yellow precipitate was filtered, stirred in water (550 mL) for 3 hours, and refiltered. The product was purified by recrystallization (ethanol) to provide yellow crystals (yield: 51.55 g; 57%). M.p.=163–167° C.

$^1$H NMR (300 MHz, $d_6$-DMSO) $\delta$2.42 (s, 3H), 6.97 (d, J=9 Hz, 2H), 7.08 (d, J=9 Hz, 2H), 7.2 (d, J=7 Hz, 4H), 7.72 (s, 1H), 12.68 (bs, 1H).

MS (DCI/NH$_3$) m/e 289 (M+H)$^+$.

EXAMPLE 2

4-Fluorophenyl-4'-methylthiobenzylketone

A solution of 2-(4-fluorophenyl)-4-methylthio-trans-cinnamic acid, prepared in Example 1, (51.48 g, 0.179 mol.)

in thionyl chloride (115 mL) was heated at reflux for 1.5 hours and then stirred at room temperature for an additional 18 hours. The reaction mixture was concentrated in vacuo, dissolved in acetone, and added dropwise to a solution of sodium azide (12.8 g, 0.197 mol.) in water (95 mL) maintained at 0° C. The mixture was allowed to warm to room temperature, diluted with water (730 mL), and extracted with toluene (1 L). The organic extract was washed with brine, dried over $MgSO_4$, and filtered. The filtrate was heated at reflux for 1.5 hours, concentrated in vacuo, and dissolved in acetic acid:water (127 mL:63 mL). The solution was heated at reflux for 2 hours, allowed to cool to room temperature, diluted with water (180 mL), whereafter a yellow solid precipitated, and was filtered. The yellow precipitate was purified by recrystallization (ethanol) to provide yellow crystals (yield: 27.85 g; 59%).

$^1$H NMR (300 MHz, $CDCl_3$) δ3.05 (s, 3H), 5.43 (s, 2H), 6.95 (m, 3H), 7.1 (m, 2H), 7.3 (d, J=9 Hz, 2H), 7.37 (m, 3H), 7.55 (m, 2H), 7.9 (d, J=9 Hz, 2H).

MS (DCl/$NH_3$) m/e 435 (M+H)$^+$, 452 (M+$NH_4$)$^+$.

Elemental analysis, calculated for $C_{24}H_{19}FN_2O_3S$: C, 66.34; H, 4.40; N, 6.44. Found: C, 66.21; H, 4.35; N, 6.43.

EXAMPLE 3

3-(4-Fluorobenzoyl)-3-(4-methylthiophenyl) propionic acid, ethyl ester

A solution of 4-fluorophenyl-4'-methylthiobenzylketone, prepared in Example 2, (10 g, 38.45 mmol.) in THF (300 mL), was prepared and maintained at −78° C. A 1M THF solution of sodium bis(trimethylsilyl)amide (38.45 mL, 38.45 mmol.) was added dropwise. The reaction mixture was stirred at −78° C. for 45 minutes and ethyl bromoacetate (4.26 mL, 38.45 mmol.) was added dropwise maintaining the temperature at −78° C. The mixture was allowed to warm to room temperature and stirred for 18 hours. The solution was acidified with a 10% citric acid solution, extracted with ether (3×50 mL), washed with brine, dried over $MgSO_4$, and concentrated in vacuo. The residue was purified by chromatography (silica gel, 5% ethyl acetate/hexane) to provide an oil (yield: 8.7 g; 65%).

$^1$H NMR (300 MHz, $d_6$-DMSO) δ1.1 (s, 3H), 2.41 (s, 3H), 2.66 & 2.71 (2d, j=5 Hz, 1H), 3.14 & 3.20 (2d, J=5 Hz, 1H), 4.02 (q, J=7 Hz, 2H), 5.19 & 5.23 (2d, J=5 Hz, 1H), 7.18 (d, J=9 Hz, 2H), 7.29 (m, 4H), 8.1 (m, 2H).

MS (DCl/$NH_3$) m/e 347 (M+H)$^+$.

EXAMPLE 4

3-(4-Fluorobenzoyl)-3-(4-methylsulfonylphenyl) propionic acid, ethyl ester

To a stirred solution of ethyl 3-(4-fluorobenzoyl)-3-(4'-methylthiophenyl)propionate, prepared in Example 3 (8.7 g, 25.11 mmol.), in $CH_2Cl_2$ (450 mL) at 0° C. was added 3-chloroperoxybenzoic acid (17.3 g, 50.22 mmol.). The reaction mixture was warmed to room temperature and stirred for 45 minutes. The solution was quenched with a saturated aqueous solution of sodium sulfite. The organic layer was washed with 1N aqueous NaOH (2×50 mL), brine, and dried over $MgSO_4$. The solution was concentrated in vacuo to provide an oil (yield: 9.45 g; 99%).

$^1$H NMR (300 MHz, $d_6$-DMSO) δ1.1 (t, J=7 Hz, 3H), 2.76 & 2.82 (2d, J=5 Hz, 1H), 3.17 (s, 3H), 3.18–3.32 (m, 1H), 4.03 (q, J=7 Hz, 2H), 5.42 & 5.45 (2d, J=5 Hz, 1H), 7.32 (t, J=9 Hz, 3H), 7.65 (d, J=9 Hz, 2H), 7.84 (d, J=9 Hz, 2H), 8.16 (dd, J=9 Hz, 7 Hz, 2H).

MS (DCl/$NH_3$) m/e 379 (M+H)$^+$.

EXAMPLE 5

5-(4-Methylsulfonylphenyl)-6-(4-fluorophenyl)-4,5-dihydro-3(2H)-pyridazinone

To a stirred solution of ethyl 3-(4-fluorobenzoyl)-3-(4-methylsulfonylphenyl)propionate, prepared in Example 3 (9.7 g, 26.99 mmol.), in ethanol (140 mL) was added hydrazine monohydrate (40 mL, 0.824 mol.). The reaction vessel was equipped with a soxhelet extractor, heated at reflux for 7 hours. The reaction mixture was concentrated in vacuo, quenched with ice water (100 mL) and concentrated HCl (10 mL), extracted with ethyl acetate (3×50 mL). The combined extracts were washed with brine, dried over $MgSO_4$, and concentrated in vacuo. The product was purified by recrystallization (MeOH) to provide a yellow solid (yield: 3.79 g; 41%). M.p.=240–241° C.

$^1$H NMR (300 MHz, $CDCl_3$) δ2.8 (m, 1H), 3.05 (s, 3H), 3.1 (m, 1H), 4.58 (m, 1H), 7.05 (t, J=9 Hz, 2H), 7.42 (d, J=9 Hz, 2H), 7.65 (m, 2H), 7.91 (d, J=9 Hz, 2H), 8.88 (bs, 1H).

MS (DCl/$NH_3$) m/e 347 (M+H)$^+$.

EXAMPLE 6

5-(4-Methylsulfonylphenyl)-6-(4-fluorophenyl)-3 (2H)-pyridazinone

To a stirred solution of 5-(4-methylsulfonylphenyl)-6-(4-fluorophenyl)-4,5-dihydro-3(2H)-pyridazinone, prepared in Example 5 (2.6 g, 7.51 mmol.), in glacial acetic acid (250 mL) maintained at 95° C. was added bromine (0.386 mL, 7.51 mmol.). The reaction mixture was stirred at 95° C. for 30 minutes, concentrated in vacuo, quenched with water, and extracted with ethyl acetate (2×25 mL). The combined extracts were washed with brine, dried over $MgSO_4$, concentrated in vacuo, and filtered to provide a yellow solid (yield: 2.13 g; 82%). M.p.=260–262° C.

$^1$H NMR (300 MHz, $CDCl_3$) δ3.08 (s, 3H), 6.98 (m, 3H), 7.13 (m, 2H), 7.35 (d, J=9 Hz, 2H), 7.92 (d, J=9 Hz, 2H), 11.1 (bs, 1H).

MS (DCl/$NH_3$) m/e 345 (M+H)$^+$.

EXAMPLE 7

2-Benzyl-5-(4-methylsulfonylphenyl)-6-(4-fluorophenyl)-3(2H)-pyridazinone

A solution of 5-(4-methylsulfonylphenyl)-6-(4-fluorophenyl)-3(2H)-pyridazinone, prepared in Example 6 (600 mg, 1.74 mmol.), $K_2CO_3$ (264 mg, 1.91 mmol.), benzyl bromide (0.207 mL, 1.74 mmol.) and NaI (about 0.1 eq., catalytic) in about 40 mL of dimethylformamide was stirred at room temperature for 18 hours. The reaction mixture was quenched with 2N HCl, and extracted with ethyl acetate (2×20 mL). The combined extracts were washed with brine, water, and dried over $MgSO_4$. The dried extracts were concentrated in vacuo and the residue purified by recrystallization (MeOH) to provide a white solid (yield: 601 mg; 79%). M.p.=172–174° C.

$^1$H NMR (300 MHz, $CDCl_3$) δ3.05 (s, 3H), 5.43 (s, 2H), 6.95 (m, 3H), 7.1 (m, 2H), 7.3 (d, J=9 Hz, 2H), 7.37 (m, 3H), 7.55 (m, 2H), 7.9 (d, J=9 Hz, 2H).

MS (DCl/$NH_3$) m/e 435 (M+H)$^+$, 452 (M+$NH_4$)$^+$.

Elemental analysis, calculated for $C_{24}H_{19}FN_2O_3S$: C, 66.34; H, 4.40; N, 6.44. Found: C, 66.21; H, 4.35; N, 6.43.

EXAMPLE 8

2-Methyl-5-(4-methylsulfonylphenyl)-6-(4-fluorophenyl)-3(2H)-pyridazinone

The title compound was prepared according to the method of Example 7, substituting methyl iodide for benzyl bromide. M.p.=181–182° C.

¹H NMR (300 MHz, CDCl₃) δ3.08 (s, 3H), 3.92 (s, 3H), 6.98 (m, 3H), 7.13 (m, 2H), 7.32 (d, J=9 Hz, 2H), 7.9 (d, J=9 Hz, 2H).

MS (DCl/NH₃) m/e 359 (M+H)⁺, 376 (M+NH₄)⁺.

Elemental Analysis: calculated for $C_{18}H_{15}FN_2O_3S$: C, 60.32; H, 4.21; N, 7.81. Found: C, 60.26; H, 3.93; N, 7.81.

EXAMPLE 9

2-Ethyl-5-(4-methylsulfonylphenyl)-6-(4-fluorophenyl)-3(2H)-pyridazinone

The title compound was prepared according to the method of Example 7, substituting ethyl bromide for benzyl bromide. M.p.=177–179° C.

¹H NMR (300 MHz, CDCl₃) δ1.47 (t, J=7 Hz, 3H), 3.05 (s, 3H), 4.33 (q, J=7 Hz, 2H), 6.96 (m, 3H), 7.13 (m, 2H), 7.32 (d, J=9 Hz, 2H), 7.9 (d, J=9 Hz, 2H).

MS (DCl/NH₃) m/e 373 (M+H)⁺, 390 (M+NH₄)⁺.

Elemental analysis, calculated for $C_{19}H_{17}FN_2O_3S \cdot 0.25M\ H_2O$: C, 60.54; H, 4.67; N, 7.43; Found: C, 60.40; H, 4.55; N, 7.43.

EXAMPLE 10

2-(4-Fluorobenzyl)-5-(4-methylsulfonylphenyl)-6-(4-fluorophenyl)-3(2H)-pyridazinone The title compound was prepared according to the method of Example 7, substituting 4-fluorobenzyl bromide for benzyl bromide. M.p.=150–151° C.

¹H NMR (300 MHz, CDCl₃) δ3.05 (s, 3H), 5.4 (s, 2H), 6.92–7.14 (m, 7H), 7.3 (d, J=9 Hz, 2H), 7.52 (m, 2H), 7.9 (d, J=9 Hz, 2H).

MS (DCl/NH₃) m/e 453 (M+H)⁺, 470 (M+NH₄)⁺.

Elemental Analysis: calculated for $C_{24}H_{18}F_2N_2O_3S$: C, 63.70; H, 4.00; N, 6.19. Found: C, 63.46; H, 3.86; N, 5.92.

EXAMPLE 11

2-(n-Butyl)-5-(4-methylsulfonylphenyl)-6-(4-fluorophenyl)-3(2H)-pyridazinone

The title compound was prepared according to the method of Example 7, substituting n-butyl bromide for benzyl bromide. M.p.=111–113° C.

¹H NMR (300 MHz, CDCl₃) δ1.0 (t, J=7 Hz, 3H), 1.47 (m, 2H), 1.9 (m, 2H), 3.08 (s, 3H), 4.28 (t, J=7 Hz, 2H), 6.96 (m, 3H), 7.14 (m, 2H), 7.33 (d, J=9 Hz, 2H), 7.9 (d, J=9 Hz, 2H).

MS (DCl/NH₃) m/e 401 (M+H)⁺, 418 (M+NH₄)⁺.

Elemental Analysis: calculated for $C_{21}H_{21}FN_2O_3S$: C, 62.98; H, 5.28; N, 6.99. Found: C, 62.95; H, 4.67; N, 6.90.

EXAMPLE 12

2-(4-Fluoro-α-methylbenzyl)-5-(4-methylsulfonylphenyl)-6-(4-fluorophenyl)-3(2H)-pyridazinone The title compound was prepared according to the method of Example 7, substituting 4-fluoro-α-methyl benzyl bromide (synthesized from 4-fluoro-α-methyl benzyl alcohol) for benzyl bromide. M.p.=185–186° C.

¹H NMR (300 MHz, CDCl₃) δ 1.84 (d, J=7 Hz, 3H), 3.07 (s, 3H), 6.43 (q, J=7 Hz, 1H), 6.91–7.11 (m, 7H), 7.31 (d, J=9 Hz, 2H), 7.52 (m, 2H), 7.9 (d, J=9 Hz, 2H).

MS (DCl/NH₃) m/e 467 (M+H)⁺, 484 (M+NH₄)⁺.

Elemental Analysis: calculated for $C_{25}H_{20}F_2N_2O_3S$: C, 64.36; H, 4.32; N, 6.00. Found: C, 64.38; H, 4.07; N, 5.93.

EXAMPLE 13

2-(n-Propyl)-5-(4-methylsulfonylphenyl)-6-(4-fluorophenyl)-3(2H)-pyridazinone

The title compound was prepared according to the method of Example 7, substituting propyl bromide for benzyl bromide. M.p.=155–157° C.

¹H NMR (300 MHz, CDCl₃) δ 1.04 (t, J=7 Hz, 3H), 1.94 (m, 2H), 3.08 (s, 3H), 4.23 (t, J=7 Hz, 2H), 6.96 (m, 3H), 7.13 (m, 2H), 7.33 (d, J=9 Hz, 2H), 7.9 (d, J=9 Hz, 2H);

MS (DCl/NH₃) m/e 387 (M+H)⁺, 404 (M+NH₄)⁺.

Elemental Analysis: calculated for $C_{20}H_{19}FN_2O_3S$: C, 62.16; H, 4.95; N, 7.24. Found: C, 62.15; H, 4.78; N, 7.22.

EXAMPLE 14

2-(n-Pentyl)-5-(4-methylsulfonylphenyl)-6-(4-fluorophenyl)-3(2H)-pyridazinone

The title compound was prepared according to the method of Example 7, substituting n-pentyl bromide for benzyl bromide. M.p.=65–67° C.

¹H NMR (300 MHz, CDCl₃) δ 0.93 (m, 3H), 1.2 (m, 4H), 1.9 (m, 2H), 3.08 (s, 3H), 4.28 (t, J=7 Hz, 2H), 6.97 (m, 3H), 7.14 (m, 2H), 7.33 (d, J=9Hz, 2H), 7.9 (d, J=9 Hz, 2H).

MS (DCl/NH₃) m/e 415 (M+H)⁺, 432 (M+NH₄)⁺.

Elemental Analysis: calculated for $C_{22}H_{23}FN_2O_3S \cdot 0.75M\ H_2O$: C, 61.73; H, 5.76; N, 6.54. Found: C, 61.97; H, 6.00; N, 6.36.

EXAMPLE 15

2-Cyclohexylmethyl-5-(4-methylsulfonylphenyl)-6-(4-fluorophenyl)-3(2H)-pyridazin-one The title compound was prepared according to the method of Example 7, substituting cyclohexylmethyl bromide for benzyl bromide. M.p.=175–176° C.

¹H NMR (300 MHz, CDCl₃) δ 1.03–1.38 (m, 5H), 1.63–1.8 (m, 5H), 2.05 (m, 1H), 3.08 (s, 3H), 4.13 (d, J=7 Hz, 2H), 6.97 (m, 3H), 7.14 (m, 2H), 7.33 (d, J=9 Hz, 2H), 7.9 (d, J=9 Hz, 2H).

MS (DCl/NH₃) m/e 441 (M+H)⁺, 458 (M+NH₄)⁺.

Elemental Analysis: calculated for $C_{24}H_{25}FN_2O_3S \cdot 0.25M\ H_2O$: C, 64.77; H, 5.77; N, 6.29. Found: C, 64.63; H, 5.85; N, 6.16.

EXAMPLE 16

2-Phenacyl-5-(4-methylsulfonylphenyl)-6-(4-fluorophenyl)-3(2H)-pyridazinone

The title compound was prepared according to the method of Example 7, substituting 2-bromoacetophenone for benzyl bromide. M.p.=178–180° C.

¹H NMR (300 MHz, CDCl₃) δ 3.08 (s, 3H), 5.75 (s, 2H), 6.96 (t, J=9 Hz, 2H), 7.03 (s, 1H), 7.15 (dd, J=9 Hz, 7 Hz, 2H), 7.37 (d, J=9 Hz, 2H), 7.55 (t, J=7 Hz, 2H), 7.68 (t, J=7 Hz, 1H), 7.94 (d, J=9 Hz, 2H), 8.05 (d, J=7 Hz, 2H).

MS (DCl/NH₃) m/e 463 (M+H)⁺, 480 (M+NH₄)⁺.

Elemental Analysis: calculated for $C_{25}H_{19}FN_2O_4S \cdot 0.75\ M\ H_2O$: C, 63.08; H, 4.34; N, 5.88. Found: C, 63.01; H, 4.12; N, 5.85.

EXAMPLE 17

2-Propargyl-5-(4-methylsulfonylphenyl)-6-(4-fluorophenyl)-3(2H)-pyridazinone

The title compound was prepared according to the method of Example 7, substituting propargyl bromide for benzyl bromide. M.p.=168–169° C.

$^1$H NMR (300 MHz, CDCl$_3$) 67 2.4 (t, J=3 Hz, 1H), 3.08 (s, 3H), 5.05 (d, J=3 Hz, 2H), 6.97 (t, J=9 Hz, 2H), 6.99 (s, 1H), 7.16 (dd, J=9 Hz, 7 Hz, 2H), 7.34 (d, J=9 Hz, 2H), 7.91 (d, J=9 Hz, 2H).

MS (DCl/NH$_3$) m/e 383 (M+H)$^+$, 400 (M+NH$_4$)$^+$.

Elemental Analysis: calculated for C$_{20}$H$_{15}$FN$_2$O$_3$S.0.25 M H$_2$O: C, 62.08; H, 4.03; N, 7.24. Found: C, 62.15; H, 4.18; N, 7.05.

EXAMPLE 18

2-Cyclohexyl-5-(4-methylsulfonylphenyl)-6-(4-fluorophenyl)-3(2H)-pyridazinone

The title compound was prepared according to the method of Example 7, substituting cyclohexyl bromide for benzyl bromide. M.p.=86–90° C.

$^1$H NMR (300 MHz, d$_6$-DMSO) 67 1.5 (m, 10H), 3.24 (s, 3H), 4.85 (m, 1H), 7.04 (s, 1H), 7.19 (m, 4H), 7.46 (d, J=9 Hz, 2H), 7.87 (d, J=9 Hz, 2H).

MS (DCl/NH$_3$) m/e 427 (M+H)$^+$.

Elemental Analysis calculated. for C$_{23}$H$_{23}$FN$_2$O$_3$S: C, 64.77; H, 5.43; N, 6.56. Found: C, 64.52; H, 5.4; N, 6.38.

EXAMPLE 19

2-(2-Butyn-1-yl)-5-(4-methylsulfonylphenyl)-6-(4-fluorophenyl)-3(2H)-pyridazinone The title compound was prepared according to the method of Example 7, substituting 1-bromo-2-butyne for benzyl bromide. M.p.=81–82° C.

$^1$H NMR (300 MHz, d$_6$-DMSO) 67 1.81 (t, J=3 Hz, 3H), 3.24 (s, 3H), 4.93 (d, J=3,2H), 7.10 (s, 1H), 7.19 (m, 4H), 7.48 (d, J=9 Hz, 2H), 7.87 (d, J=9 Hz, 2H).

MS (DCl/NH$_3$) m/e 397 (M+H)$^+$. Elemental analysis, calculated for C$_{21}$H$_{17}$FN$_2$O$_3$S: C, 63.62; H, 4.32; N, 7.06. Found: C, 64.22; H, 4.36; N, 6.61.

EXAMPLE 20

2-(Cyclobutylmethyl)-5-(4-methylsulfonylphenyl)-6-(4-fluorophenyl)-3(2H)-pyridazinone The title compound was prepared according to the method of Example 7, substituting chloromethylcyclobutane for benzyl bromide. M.p.=74–76° C.

$^1$H NMR (300 MHz, d$_6$-DMSO) δ1.98 (m, 4H), 2.05 (m, 2H), 2.84 (p, J=7.5 Hz, 1H), 3.24 (s, 3H), 4.22 (d, J=7.5 Hz, 2H), 7.05 (s, 1H), 7.16 (m, 4H), 7.45 (d, J=9 Hz, 2H), 7.87 (d, J=9 Hz, 2H).

MS (DCl/NH$_3$) m/e 413 (M+H)$^+$.

Elemental analysis,calculated for C22H21 FN$_2$O$_3$S: C, 64.06; H, 5.13; N, 6.79. Found: C, 64.37; H, 5.26; N, 6.73.

EXAMPLE 21

2-(3-Methylbuten-2- yl)-5-(4-methylsulfonylphenyl)-6-(4-fluorophenyl)-3(2H-pyridazinone The title compound was prepared according to the method of Example 7, substituting 4-bromo-2-methyl-2-butene for benzyl bromide. M.p.=71–72° C.

$^1$H NMR (300 MHz, d$_6$-DMSO) δ1.72 (s, 3H), 1.79 (s, 3H), 3.24 (s, 3H), 4.76 (d, J=7.5 Hz, 2H), 5.42 (m, 1H), 7.04 (s, 1H), 7.17 (m, 4H), 7.46 (d, J=9 Hz, 2H), 7.87 (d, J=9 Hz, 2H).

MS (DCI/NH$_3$) m/e 413 (M+H)$^+$.

Elemental analysis, calculated for C$_{22}$H$_{21}$ FN$_2$O$_3$S: C, 64.06; H, 5.13; N, 6.79. Found: C, 64.34; H, 4.87; N, 6.51.

EXAMPLE 22

2-(2,2,2-Trifluoroethyl)-5-(4-methylsulfonylphenyl)-6-(4-fluorphenyl)-3(2H)-pyridazinone The title compound is prepared according to the method of Example 7, substituting 2-iodo-1,1,1-trifluoroethane for benzyl bromide. M.p.=177–179° C.

$^1$H NMR (300 MHz, CDCl$_3$) δ3.08 (s, 3H), 4.90 (q, 2H), 6.98 (t, J=9 Hz, 2 H), 7.01 (s, 1H), 7.13 (dd, J=9 Hz, 7 Hz, 2H), 7.34 (d, J=9 Hz, 2H), 7.92 (d, J=9 Hz, 2H).

MS (DCI/NH$_3$) m/e 427 (M+H)$^+$, 444 (M+NH$_4$)$^+$.

Elemental analysis, calculated for C$_{19}$H$_{14}$F$_3$N$_2$O$_3$S (0.25 hydrate): C, 52.96; H, 3.39; N, 6.50. Found: C, 52.89; H, 3.35; N, 6.27.

EXAMPLE 23

2-(Cyclopropylmethyl)-5-(4-methylsulfonylphenyl)-6-(4-fluorophenyl)-3(2H)-pyridazinone The title compound was prepared according to the method of Example 7, substituting cyclopropylmethyl bromide for benzyl bromide. M.p.=130–132° C.

$^1$H NMR (300 MHz, CDCl$_3$) 0.5 (m, 2H), 0.6 (m, 2H), 1.46 (m, 1H), 3.08 (s, 3H), 4.15 (d, J=7 Hz, 2H), 6.97 (s, 1H), 6.98 (d, J=9 Hz, 2H), 7.14 (dd, J=9 Hz, 7 Hz, 2H), 7.35 (d, J=9 Hz, 2H), 7.9 (d, J=9 Hz, 2H).

MS m/e 399 (M+H)$^+$, 416 (M+NH$_4$)$^+$.

Elemental analysis, calculated for C$_{21}$H$_{19}$FN$_2$O$_3$S: C, 63.30; H, 4.80; N, 7.03. Found: C, 63.13; H, 4.75; N, 6.94.

EXAMPLE 24

2-Cyclopentylmethyl-5-(4-methylsulfonylphenyl)-6-(4-fluorophenyl)-3(2H)-pyridazinone The title compound was prepared according to the method of Example 7, substituting chloromethylcyclopentane for benzyl bromide. M.p.=76–77° C.

$^1$H NMR (d$_6$-DMSO, 300 MHz) δ1.38 (m, 2H), 1.6 (m, 7H), 3.23 (s, 3H), 4.11 (d, J=7.5 Hz, 2H), 7.05 (s, 1H), 7.17 (m, 4H), 7.47 (d, J=9 Hz, 2H), 7.87 (d, J=9 Hz, 2H).

MS (DCI/NH$_3$) m/e 427 (M+H)$^+$.

Elemental analysis, calculated for C$_{23}$H$_{23}$FN$_2$O$_3$S: C, 64.77; H, 5.43; N, 6.56. Found: C, 63.96; H, 5.11; N, 6.44.

EXAMPLE 25

2-Cyclopentyl-5-(4-methylsulfonylphenyl)-6-(4-fluorophenyl)-3(2H)-pyridazinone

The title compound was prepared according to the method of Example 7, substituting chlorocyclopentane for benzyl bromide. M.p.=191–192° C.

¹H NMR (d₆-DMSO, 300 MHz) δ1.65 (m, 2H), 1.85 (m, 4H), 2.05 (m, 2H), 3.24 (s, 3H), 5.39 (p, J=7.5 Hz, 1H), 7.02 (s, 1H), 7.18 (m, 4H), 7.46 (d, J=9 Hz, 2H), 7.89 (d, J=9 Hz, 2H).

MS (DCI/NH₃) m/e 413 (M+H)⁺.

Elemental analysis, calculated for $C_{22}H_{21}FN_2O_3S$: C, 64.06; H, 5.13; N, 6.79. Found: C, 64.14; H, 5.11; N, 6.69.

Prostaglandin Inhibition Determination

Compound Preparation and Administration

For oral administration, test compounds were suspended on the day of use in 100% polyethyleneglycol (PEG 400) with a motorized homogenizer equipped with a Teflon-coated pestle (TRI-R Instrument, Jamaica, N.Y.).

To compare the mean responses of the treatment groups, analysis of variance was applied. Percent inhibition values were determined by comparing the individual treatment mean values to the mean of the control group. Linear regression was used to estimate $IC_{50}$'s/$ED_{50}$'s in appropriate assays.

EIA Determination of Prostaglandins

EIA reagents for prostaglandin determination were purchased from Perseptive Diagnostics, (Cambridge, Mass.). $PGE_2$ levels in lavage fluids were determined after the samples were dried under nitrogen and reconstituted with assay buffer. $PGE_2$ levels in enzyme assays or cell culture media were measured against standards prepared in the same milieu. The immunoassays were conducted as recommended by the manufacturer. The EIA was conducted in 96 well microtiter plates (Nunc Roskilde, Denmark) and optical density was measured using a microplate reader (Vmax, Molecular Devices Corp., Menlo Park, Calif.).

Recombinant Human PGHS-1 and PGHS-2 Enzyme Assays

Inhibition of prostaglandin biosynthesis in vitro was evaluated using recombinant human Cox-1 (r-hu Cox1) and Cox-2 (r-hu Cox2) enzyme assays. Representative compounds dissolved in DMSO (3.3 % v/v) were preincubated with microsomes from recombinant human Cox-1 or Cox-2 expressed in the baculovirus/Sf9 cell system (Gierse, J. K., Hauser, S. D., Creely, D. P., Koboldt, C., Rangwala, S. H., Isakson, P. C., and Seibert, K. *Expression and selective inhibition of the constituitive and inducible forms of cyclooxygenase, Biochem J.* 1995, 305: 479.), together with the cofactors phenol (2 mM) and hematin (1 μM) for 60 minutes prior to the addition of 10 μM arachidonic acid. The reaction was allowed to run for 2.5 minutes at room temperature prior to quenching with HCl and neutralization with NaOH. $PGE_2$ production in the presence and absence of the drug was determined by EIA analysis. The EIA was conducted in 96 well microtiter plates (Nunc Roskilde, Denmark) and optical density was measured using a microplate reader (Vmax, Molecular Devices Corp., Menlo Park, Calif.). EIA reagents for prostaglandin determination were purchased from Perseptive Diagnostics (Cambridge, Mass.). $PGE_2$ levels were measured against standards prepared in the same milieu. The immunoassays were conducted as recommended by the manufacturer.

The data illustrating the inhibition of prostaglandin biosynthesis in vitro by compounds of this invention is shown in Table 1. The compounds are designated by the Example Number. Column 2 shows Cox-1 percent inhibition at the particular micromolar dose level. Column 3 shows Cox-2 percent inhibition at the particular nanomolar dose level. Values for Cox-2 inhibition that are parenthetical indicate $IC_{50}$ values.

TABLE 1

| Example No. | RHUCX1 (μM) | RHUCX2 (nM) |
| --- | --- | --- |
| 7 | 4 @ 100 | (20) |
| 10 | 2 @ 100 | 65 @ 100 |
| 11 | 19 @ 100 | 51 @ 100 |
| 12 | 8 @ 100 | (740) |
| 14 | 23 @ 100 | 66 @ 100 |
| 15 | 52 @ 100 | (5) |
| 17 | 0 @ 100 | (850) |
| 18 | 16 @ 100 | 49 @ 100 |
| 19 | 3 @ 100 | 66 @ 1000 |
| 21 | 62 @ 100 | 92 @ 100 |
| 22 | 0 @ 100 | 46 @ 1000 |
| 23 | 24 @ 100 | (250) |
| 24 | 23 @ 100 | 87 @ 100 |
| 25 | 7 @ 100 | 42 @ 100 |

IL-1β Induced $PGE_2$ Production in WISH Cells

Human amnionic WISH cells were grown to 80% confluence in 48 well plates. Following removal of the growth medium and two washings with Gey's 10 Balanced Salt Solution, 5 ng IL-1β/ml (UBI, Lake Placid, N.Y.) was added to the cells with or without test compound in DMSO (0.01% v/v) in Neuman-Tytell Serumless Medium (GIBCO, Grand Island, N.Y.). Following an 18 hour incubation to allow for the maximal induction of PGHS-2, the conditioned medium was removed and assayed for $PGE_2$ activity by EIA analysis as described above.

U937 (ATCC, Rockville, Md.) cells were grown in a similar fashion to the WISH cells. After incubation, the conditioned medium was removed and assayed for Cox-1 activity by EIA analysis as described above.

The data illustrating the inhibition of prostaglandin biosynthesis in vitro by compounds of this invention is shown in Table 2. U937 values indicate percent inhibition at the particular micromolar dose level while parenthetical values indicate $IC_{50}$ values. Wish cell values indicate Cox-2 pecent inhibition at the particular micromolar dose level.

TABLE 2

| Example No. | U937 (μM) | Wish (mM) |
| --- | --- | --- |
| 7 | (0.87) | (0.02) |
| 10 | 62 @ 10 | (0.11) |
| 14 | 42 @ 1 | 34 @ 0.00001 |
| 15 | 33 @ 0.01 | 43 @ 0.001 |
| 17 | 41 @ 10 | 54 @ 1 |
| 20 | 60 @ 10 | (0.13) |
| 21 | 80 @ 10 | (0.00004) |
| 23 | 30 @ 10 | 62 @ 1 |

Carrageenan Induced Paw Edema (CPE) in Rats

Hindpaw edema was induced in male rats as described by Winter et al., *Proc. Soc. Exp. Biol. Med.,* 1962, 111, 544. Briefly, male Sprague-Dawley rats weighing between 170 and 190 g were administered test compounds orally 1 hour prior to the subplantar injection of 0.1 ml of 1% sodium carrageenan (lambda carrageenan, Sigma Chemical Co., St Louis, Mo.) into the right hindpaw. Right paw volumes (ml) were measured immediately following injection of carrageenan for baseline volume measurements using a Buxco plethysmograph (Buxco Electronics, Inc., Troy, N.Y.). Three hours after the injection of carrageenan, right paws were remeasured and paw edema calculated for each rat by subtracting the zero time reading from the 3 hour reading. Data are reported as mean percent inhibition +/− SEM.

Statistical significance of results was analyzed by Dunnetts multiple comparison test where p<0.05 was considered statistically significant.

Rat Carrageenan Pleural Inflammation Model (CIP)

Pleural inflammation was induced in male adrenalectomized Sprague-Dawley rats following the method of Vinegar et al., *Fed. Proc.* 1976, 35, 2447–2456. Animals were orally dosed with experimental compounds, in 0.2% HPMC, 30 minutes prior to the intrapleural injection of 2% lambda carrageenan (Sigma Chemical Co., St. Louis Mo.). Four hours later the animals were euthanized and the pleural cavities lavaged with ice cold saline. The lavage fluid was then added to two volumes of ice cold methanol (final methanol concentration 66%) to lyse cells and precipitate protein. Eicosanoids were determined by EIA as described above. The data illustrating the inhibition of prostaglandin biosynthesis in vivo by the compounds of this invention is shown in Table 3. Values reported are percent inhibition at 10 milligrams per kilogram body weight.

TABLE 3

| Example No. | CIP Inh @ 10 mpk |
| --- | --- |
| 7 | 22 |
| 23 | 41 |

Pharmaceutical Compositions

The present invention also provides pharmaceutical compositions which comprise compounds of the present invention formulated together with one or more non-toxic pharmaceutically acceptable carriers. The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the procedures and judgements well known to one skilled in the art. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

The compounds of the present invention may be potentially useful in the treatment of several illness or disease states such as inflammatory diseases, dysmennorhea, asthma, premature labor, osteoporosis, and ankylosing spondolitis. Current Drugs Ltd, ID Patent Fast Alert, AG16, May 9, 1997.

The compounds of the present invention may also be potentially useful in the treatment of cancers, and in particular, colon cancer. Proc. Natl. Acad. Sci., 94, pp. 3336–3340, 1997.

The compounds of the present invention may be useful by providing a pharmaceutical composition for inhibiting prostaglandin biosynthesis comprising a therapeutically effective amount of a compound of formula I or a pharmaceutically acceptable salt, ester, or prodrug thereof, and a pharmaceutically acceptable carrier.

The compounds of the present invention may be useful by providing a pharmaceutical composition for inhibiting prostaglandin biosynthesis comprising a therapeutically effective amount of a compound of formula II or a pharmaceutically acceptable salt, ester, or prodrug thereof, and a pharmaceutically acceptable carrier.

The compounds of the present invention may be useful by providing a pharmaceutical composition for inhibiting prostaglandin biosynthesis comprising a therapeutically effective amount of a compound of formula III or a pharmaceutically acceptable salt, ester, or prodrug thereof, and a pharmaceutically acceptable carrier.

The compounds of the present invention may be useful by providing pharmaceutical composition for inhibiting prostaglandin biosynthesis comprising a therapeutically effective amount of a compound of formula IV or a pharmaceutically acceptable salt, ester, or prodrug thereof, and a pharmaceutically acceptable carrier.

In addition, the compounds of the present invention may be useful by providing a method for inhibiting prostaglandin biosynthesis comprising administering to a mammal in need of such treatment a therapeutically effective amount of a compound of formula I or a pharmaceutically acceptable salt, ester, or prodrug thereof.

The compounds of the present invention may be useful by providing a method for inhibiting prostaglandin biosynthesis comprising administering to a mammal in need of such treatment a therapeutically effective amount a compound of formula II or a pharmaceutically acceptable salt, ester, or prodrug thereof.

The compounds of the present invention may be useful by providing a method for inhibiting prostaglandin biosynthesis comprising administering to a mammal in need of such treatment a therapeutically effective amount compound of formula III or a pharmaceutically acceptable salt, ester, or prodrug thereof.

The compounds of the present invention may be useful by providing a method for inhibiting prostaglandin biosynthesis comprising administering to a mammal in need of such treatment a therapeutically effective amount a compound of formula IV or a pharmaceutically acceptable salt, ester, or prodrug thereof.

In addition, the compounds of the present invention may be useful by providing a method for treating pain, fever, inflamation, rheumatoid arthritis, osteoarthritis, and cancer comprising administering to a mammal in need of such treatment a therapeutically effective amount of a compound of formula I.

In addition, the compounds of the present invention may be useful by providing a method for treating pain, fever, inflamation, rheumatoid arthritis, osteoarthritis,and cancer comprising administering to a mammal in need of such treatment a therapeutically effective amount of a compound of formula II.

In addition, the compounds of the present invention may be useful by providing a method for treating pain, fever, inflamation, rheumatoid arthritis, osteoarthritis,and cancer comprising administering to a mammal in need of such treatment a therapeutically effective amount of a compound of formula III.

In addition, the compounds of the present invention may be useful by providing a method for treating pain, fever, inflamation, rheumatoid arthritis, osteoarthritis,and cancer comprising administering to a mammal in need of such treatment a therapeutically effective amount of a compound of formula IV.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (such as, for example, cottonseed, groundnut, corn, germ, olive, castor, sesame oils, and the like), glycerol, tetrahydrofurfuryl alcohol, poly-ethyl-ene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, such as, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, such as, for example, a solution in 1,3-butanediol. Among the acceptable vehicles and solvents that may be employed are water, Ringer's solution, isotonic sodium chloride solution, and the like. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectable preparations.

The injectable formulations can be sterilized by any method known in the art, such as, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and thus melt in the rectum or vaginal cavity and release the active compound.

Solid dosage forms for oral administration include capsules, tablets, pills, powders, and granules. In such solid dosage forms, the active compound is usually mixed with at least one inert, pharmaceutically acceptable excipient or carrier such as, for example, sodium citrate or dicalcium phosphate and/or a) fillers or extenders such as, for example, starches, lactose, sucrose, glucose, mannitol, and silicic acid, b) binders such as, for example, carboxymethylcellulose, alginates, gelatin, polyvinylpyrrolidinone, sucrose, and acacia, c) humectants such as, for example, glycerol, d) disintegrating agents such as, for example, agar-agar, calcium carbonate, potato or tapioca starch, alginic acid, certain silicates, and sodium carbonate, e) solution retarding agents such as, for example, paraffin, f) absorption accelerators such as, for example, quaternary ammonium compounds, g) wetting agents such as, for example, cetyl alcohol and glycerol monostearate, h) absorbents such as, for example, kaolin and bentonite clay, and) lubricants such as, for example, talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients such as, for example, lactose or milk sugar as well as high molecular weight polyethylene glycols and the like.

Solid compositions of a similar type may also be employed as fillers in soft and hard-filled gelatin capsules using excipients such as, for example, lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulation art. In such solid dosage forms the active compound may be admixed with at least one inert diluent such as, for example, sucrose, lactose or starch. Such dosage forms may also comprise, as is normal. practice, additional substances other than inert diluents, e.g., tableting lubricants and other tableting aids such as, for example, magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as, for example, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as, for example, lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in a suitable medium. Absorption enhancers can also be used to increase the flux of the compound across the skin. The rate can be controlled by either providing a rate controlling membrane or by dispersing the compound in a polymer matrix or gel.

According to the methods of treatment of the present invention, a patient, such as a human or mammal, is treated by administering to the patient a therapeutically effective amount of a compound of the invention, in such amounts and for such time as is necessary to achieve the desired result. By a "herapeutically effective amount" of a compound of the invention is meant a sufficient amount of the compound to provide the relief desired, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.001 to about 1000 mg/kg body weight daily or more preferably from about 0.1 to about 100 mg/kg body weight for oral administration or 0.01 to about 10 mg/kg for parenteral administration daily. Single dose compositions may contain such amounts or submultiples thereof to make up the daily dose.

The amount of active ingredient that may be combined with the carrier materials to produce a single dosage form will vary depending upon the host treated and the particular mode of administration.

The reagents required for the synthesis of the compounds of the invention are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA); Alfa Aesar (Ward Hill, Mass. 01835-9953); Eastman Chemical Company (Rochester, N.Y. 14652-3512); Lancaster Synthesis Inc. (Windham, N.H. 03087-9977); Spectrum Chemical Manufacturing Corp. (Janssen Chemical) (New Brunswick, N.J. 08901); Pfaltz and Bauer (Waterbury, Conn. 06708). Compounds which are not commercially available can be prepared by employing known methods from the chemical literature.

We claim:

1. A compound of formula I:

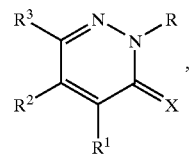

or a pharmaceutically acceptable salt thereof, wherein:

X is selected from the group consisting of O;

R is selected from the group consisting of alkyl, haloalkyl, haloalkenyl, aryl, and arylalkyl, wherein aryl in said aryl and arylalkyl groups is unsubstituted phenyl or phenyl substituted with a substituent selected from the group consisting of halogen, alkyl, and haloalkyl;

$R^2$ is a group having the formula:

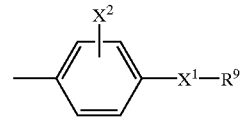

where $X^1$ is —$SO_2$—;

$R^9$ is selected from the group consisting of alkyl and amino;

$X^2$ is hydrogen;

$R^1$ is hydrogen; and $R^3$ is selected from the group consisting of hydroxyalkyl, alkyl, and aryl, wherein aryl is unsubstituted phenyl or phenyl substituted with a substituent selected from the group consisting of halogen, alkyl, alkoxy, and hydroxyalkyl; or a pharmaceutically acceptable salt thereof.

2. A compound according to claim 1 wherein:

$R_3$ is selected from unsubstituted phenyl and phenyl substituted with one, two, or three substituents wherein the substituents are selected from the group consisting of alkyl, alkoxy, fluorine and chlorine; or a pharmaceutically acceptable salt thereof.

3. A compound according to claim 1, selected from the group consisting of:

2-Benzyl-5-(4-methylsulfonylphenyl)-6-(4-fluorophenyl)-3 (2H)-pyridazinone;

2-Methyl-5-(4-methylsulfonylphenyl)-6-(4-fluorophenyl)-3 (2H)-pyridazinone;

2-Ethyl-5-(4-methylsulfonylphenyl)-6-(4-fluorophenyl)-3 (2H)-pyridazinone;

2-(4-Fluorobenzyl)-5-(4-methylsulfonylphenyl)-6-(4-fluorophenyl)-3(2H)-pyridazinone;

2-(n-Butyl)-5-(4-methylsulfonylphenyl)-6-(4-fluorophenyl)-3(2H)-pyridazinone;

2-(2,2,2-Trifluoroethyl)-5-(4-methylsulfonylphenyl)-6-(4-flurophenyl)-3(2H)-pyridazinone;

2-(4-Fluoro-α-methylbenzyl)-5-(4-methylsulfonylphenyl)-6-(4-fluorophenyl)-3(2H)-pyridazinone;

2-(n-Propyl)-5-(4-methylsulfonylphenyl)-6-(4-fluorophenyl)-3 (2H)-pyridazinone;

2-(n-Pentyl)-5-(4-methylsulfonylphenyl)-6-(4-fluorophenyl)-3(2H)-pyridazinone;

2-Cyclohexylmethyl-5-(4-methylsulfonylphenyl)-6-(4-fluorophenyl)-3(2H)-pyridazinone;

2-Phenacyl-5-(4-methylsulfonylphenyl)-6-(4-fluorophenyl)-3(2H)-pyridazinone;

2-Propargyl-5-(4-methylsulfonylphenyl)-6-(4-fluorophenyl)-3(2H)-pyridazinone;

2-Cyclohexyl-5-(4-methylsulfonylphenyl)-6-(4-fluorophenyl)-3(2H)-pyridazinone;

2-(2-Butynyl)-5-(4-methylsulfonylphenyl)-6-(4-fluorophenyl)-3(2H)-pyridazinone;

2-(Cyclobutanylmethyl)-5-(4-methylsulfonylphenyl)-6-(4-fluorophenyl)-3(2H)-pyridazinone; and 2-(3-Methylbuten-2-yl)-5-(4-methylsulfonylphenyl)-6-(4-fluorophenyl)-3(2H)-pyridazinone; or a pharmaceutically acceptable salt or ester thereof.

4. A method for treating one or more conditions selected from the group consisting of pain, fever, inflammation, rheumatoid arthritis, and osteoarthritis in a mammal comprising administering to a mammal in need of such treatment a compound of claim 1.

* * * * *

UNITED STATES PATENT AND TRADEMARK OFFICE
CERTIFICATE OF CORRECTION

PATENT NO.    : 6,525,053 B1
DATED         : February 25, 2003
INVENTOR(S)   : Lawrence A. Black It is certified that error appears in the above-identified patent and that said Letters Patent is hereby corrected as shown below:

<u>Title page,</u>
Item [57], ABSTRACT,
Line 1, replace "pyridazione" with -- pyridazinone --
Line 3, put a "." after the first appearance of the word -- inhibitors --.

Signed and Sealed this

Twenty-eighth Day of October, 2003

JAMES E. ROGAN
*Director of the United States Patent and Trademark Office*